(12) United States Patent
Watanabe et al.

(10) Patent No.: US 7,759,489 B2
(45) Date of Patent: Jul. 20, 2010

(54) TRANSITION METAL COMPLEX COMPOUND AND ORGANIC ELECTROLUMINESCENCE DEVICE USING THE COMPOUND

(75) Inventors: Masami Watanabe, Chiba (JP); Toshikazu Hirao, Hyogo (JP); Toshiyuki Moriuchi, Osaka (JP); Lisheng Mao, Shanghai (CN); Hsyueh-Liang Wu, Osaka (JP)

(73) Assignees: Idemitsu Kosan Co., Ltd., Tokyo (JP); Osaka University, Suita-shi (JP)

( * ) Notice: Subject to any disclaimer, the term of this patent is extended or adjusted under 35 U.S.C. 154(b) by 962 days.

(21) Appl. No.: 11/516,585

(22) Filed: Sep. 7, 2006

(65) Prior Publication Data

US 2007/0176540 A1 Aug. 2, 2007

(30) Foreign Application Priority Data

Jan. 27, 2006 (JP) .............................. 2006-019794
Jun. 26, 2006 (JP) .............................. 2006-175427

(51) Int. Cl.
*C07F 15/00* (2006.01)
*H05B 33/14* (2006.01)

(52) U.S. Cl. ............................ 546/2; 428/690; 428/917
(58) Field of Classification Search ...................... 546/2; 428/690, 917
See application file for complete search history.

(56) References Cited

U.S. PATENT DOCUMENTS

| | | | |
|---|---|---|---|
| 5,391,661 A | 2/1995 | Naganuma et al. | |
| 5,461,127 A | 10/1995 | Naganuma et al. | |
| 5,629,398 A | 5/1997 | Okamoto et al. | |
| 5,648,443 A | 7/1997 | Okamoto et al. | |
| 5,693,728 A | 12/1997 | Okamoto et al. | |
| 5,854,165 A | 12/1998 | Yabunouchi et al. | |
| 6,171,994 B1 | 1/2001 | Yabunouchi et al. | |
| 6,339,135 B1 | 1/2002 | Kashiwamura et al. | |
| 6,462,154 B1 | 10/2002 | Naganuma et al. | |
| 6,555,633 B1 | 4/2003 | Tanaka et al. | |
| 6,787,499 B2 | 9/2004 | Tanaka et al. | |
| 6,841,693 B1 | 1/2005 | Watanabe et al. | |
| 2004/0259720 A1 | 12/2004 | Sato et al. | |
| 2005/0170207 A1 | 8/2005 | Ma et al. | |
| 2006/0008671 A1 | 1/2006 | Kwong et al. | |

OTHER PUBLICATIONS

U.S. Appl. No. 11/516,759, filed Sep. 7, 2006, Mashima, et al.
U.S. Appl. No. 09/830,848, filed May 2, 2001, Watanabe, et al.
U.S. Appl. No. 09/830,573, filed May 8, 2001, Sato, et al.
U.S. Appl. No. 09/762,700, filed Feb. 12, 2001, Sato, et al.
Gebhard Haberhauer, et al.; "A Widely Applicable Concept for Predictable Induction of Preferred Configuration in C3-symmetric Systems"; 2005; Chem. Commun., pp. 2799-2801.

*Primary Examiner*—Charanjit S Aulakh
(74) *Attorney, Agent, or Firm*—Oblon, Spivak, McClelland, Maier & Neustadt, L.L.P.

(57) ABSTRACT

Provided are an organic electroluminescence device having high luminous efficiency and a long emission lifetime, and a transition metal complex compound realizing the organic electroluminescence device. In the transition metal complex compound, three ligands are crosslinked with a crosslinking group having a saturated cyclic structure or a saturated polycyclic structure in a tripod manner. The organic electroluminescence device includes an organic thin film layer composed of one or multiple layers including at least a light emitting layer, the organic thin film layer being interposed between a pair of electrodes. In the organic electroluminescence device, at least one layer of the organic thin film layer contains the transition metal complex compound.

15 Claims, 7 Drawing Sheets

TRANSITION METAL COMPLEX COMPOUND AND ORGANIC ELECTROLUMINESCENCE DEVICE USING THE COMPOUND

TECHNICAL FIELD

The present invention relates to a transition metal complex compound and an organic electroluminescence device using the same, and in particular, to an organic electroluminescence device having high luminous efficiency and emitting blue light, and a novel transition metal complex compound for realizing the organic electroluminescence device.

BACKGROUND ART

An organic electroluminescence (EL) device is a spontaneous light emitting device which utilizes a principle that a fluorescent substance emits light by energy of recombination of holes injected from an anode and electrons injected from a cathode when an electric field is applied. Since an organic EL device of a laminate type driven under low electric voltage was reported by C. W. Tang et al. of Eastman Kodak Co. (for example, C. W. Tang and S. A. Vanslyke, Applied Physics Letters, Volume 51, P. 913, 1987), many studies have been conducted on organic EL devices using organic materials as constituting components. Tang et al. used tris(8-hydroxyquinolinol aluminum) for a light emitting layer and a triphenyldiamine derivative for a hole transporting layer. Advantages of the laminate structure include that the efficiency of hole injection into the light emitting layer can be increased, the efficiency of forming exciton which are formed by blocking and recombining electrons injected from the cathode can be increased, and exciton formed within the light emitting layer can be enclosed therein. For the structure of the organic EL device as in the example, a two-layered structure having a hole transporting (injecting) layer and an electron transporting and light emitting layer, a three-layered structure having a hole transporting (injecting) layer, a light emitting layer, and an electron transporting (injecting) layer, and the like are well known. To increase the efficiency of recombination of injected holes and electrons in the devices having such the laminate type structures, the structure of the device and a process for forming the device have been modified.

Known examples of the light emitting material include: a chelate complex such as a tris(8-quinolinolato)aluminum complex; a coumarin derivative; a tetraphenylbutadiene derivative; a distyrylarylene derivative; and an oxadiazole derivative. It has been reported that light in a visible region ranging from a blue color to a red color can be emitted from each of those light emitting materials, so the realization of a color display device is expected from each of them (see, for example, Patent Document 1).

In addition, in recent years, there has also been proposed that a phosphorescent material as well as a fluorescent material is used in the light emitting layer of the organic EL device (see, for example, Non-patent Document 1 and Non-patent Document 2). In this way, high luminous efficiency is achieved by utilizing a singlet state and a triplet state in excited states of the phosphorescent material in the light emitting layer of the organic EL device. When an electron and a hole recombine in the organic EL device, singlet excitons and triplet excitons are considered to be produced at a ratio of 1:3 owing to a difference in spin multiplicity. Accordingly, the use of a phosphorescent light emitting material is considered to achieve luminous efficiency three to four times that of a device using only the fluorescent material.

A constitution in which layers are sequentially laminated, for example, an anode, a hole transporting layer, an organic light emitting layer, an electron transporting layer (hole inhibiting layer), an electron transporting layer, and a cathode in the stated order has been used in such the organic EL device in order that a triplet excited state or a triplet exciton does not quench. A host compound and a phosphorescent compound have been used in the organic light emitting layer (see, for example, Patent Document 2 and Patent Document 3). Those patent documents relate to techniques each concerning a phosphorescent material emitting light having a color ranging from a red color to a green color. A technique concerning a light emitting material having a blue-based luminescent color has also been published (see, for example, Patent Document 4, Patent Document 5, and Patent Document 6). However, a device using any one of those materials has an extremely short lifetime. In particular, Patent Documents 7 and 8 each describe a ligand skeleton in which an Ir metal and a phosphorus atom are bonded to each other. The ligand skeleton described in each of those documents turns a luminescent color into a blue color, but a bonding force between the metal and the atom is so weak that the ligand skeleton is remarkably poor in heat resistance. Patent Document 7 similarly describes a complex in which an oxygen atom and a nitrogen atom are bonded to a central metal, but has no description concerning a specific effect of a group to be bonded to the oxygen atom, so the effect is unclear. Patent Document 8 discloses a complex in which nitrogen atoms in different ring structures are bonded one by one to a central metal. A device using the complex emits blue light, but has an external quantum efficiency as low as around 5%.

Meanwhile, research has been conducted on a transition metal complex compound having a metal carbene bond (which may hereinafter be referred to as "carbene complex") in recent years (see, for example, Patent Documents 9 to 18 and Non-patent Documents 3 to 11).

The term "carbene" refers to dicoordination carbon having two electrons in an $sp^2$ hybrid orbital or a 2p orbital. The carbene can take four kinds of structures depending on a combination of an orbital which the two electrons enter and the orientation of a spin. The carbene is typically singlet carbene composed of an $sp^2$ hybrid, occupied orbital, and an empty 2p orbital.

A carbene complex, which has a short lifetime and is unstable, has been conventionally used as a synthesis conversion agent to be added to a reaction intermediate or olefin of an organic synthesis reaction. In about 1991, a stable carbene complex composed of a heteroaromatic ring structure and a stable carbene complex composed of a non-aromatic ring structure were found. Further, after that, it has been found that a non-cyclic carbene complex can be stably obtained by stabilization with nitrogen and phosphorus. In addition, the performance of a catalyst can be improved by bonding the non-cyclic carbene complex as a ligand to a transition metal. Accordingly, in a catalytic reaction in organic synthesis, expectations on a stable carbene complex have been raised in recent years.

In particular, in an olefin metathesis reaction, the addition or coordination of a stable carbene complex has been found to improve the performance of a catalyst significantly. In addition, researches on, for example, an improvement in efficiency of a Suzuki coupling reaction, the oxidation or selective hydroformylation reaction of an alkane, and an optically active carbene complex have been developed in recent years. Accordingly, the application of a carbene complex to the field of organic synthesis has been attracting attention.

In addition, specific examples of a complex having a carbene iridium bond are described in Non-patent Document 12 (tris(carbene) iridium complex composed of a non-heterocyclic carbene ligand) and Non-patent Document 13 (monodentate monocarbene iridium complex) to be described below. However, none of the documents describes the application of those complexes to, for example, the field of an organic EL device.

In addition, Patent Document 9 discloses the synthesis of an iridium complex having a carbene bond, the luminous wavelength of the complex, and the performance of a device using the complex. However, the complex has low energy efficiency and low external quantum efficiency, and its luminous wavelength is distributed to an ultraviolet region, so the complex has poor luminous efficiency. Therefore, the complex is not suitable for a light emitting device emitting light having a wavelength in a visible region such as an organic EL. In addition, the complex cannot be used in vacuum deposition because of, for example, its low decomposition temperature and its large molecular weight, and the complex decomposes upon vapor deposition, so the complex involves a problem in that an impurity is mixed upon production of a device.

Further, Patent Documents 10 to 18 describe various complexes each having a carbene bond, and each disclose a blue light emitting complex. However, the energy efficiency and external quantum efficiency of the blue light emitting complex are low, and none of the documents mentions an increase in emission lifetime.

Meanwhile, Patent Documents 19 and 20 each disclose, as a method of increasing the lifetime of a tris(2-phenylpyridine-$N,C^2$) iridium complex, the crosslinking of three 2-phenylpyridine-$N,C^2$ group sites in a tripod manner. However, the documents each report only a tripod crosslinked site having a benzene ring skeleton, so none of the documents has achieved a significant increase in lifetime of the complex. In addition, none of the documents describes a guideline for the emission of blue light.

Patent Document 1: JP-A-08-239655
Patent Document 2: U.S. Pat. No. 6,097,147
Patent Document 3: WO 01/41512
Patent Document 4: US 2001/0025108
Patent Document 5: US 2002/0182441
Patent Document 6: JP-A-2002-170684
Patent Document 7: JP-A-2003-123982
Patent Document 8: JP-A-2003-133074
Patent Document 9: WO 05/019373
Patent Document 10: US 2005/0258433
Patent Document 11: US 2005/0258742
Patent Document 12: US 2005/0260441
Patent Document 13: US 2005/0260444
Patent Document 14: US 2005/0260445
Patent Document 15: US 2005/0260446
Patent Document 16: US 2005/0260447
Patent Document 17: US 2005/0260448
Patent Document 18: US 2005/0260449
Patent Document 19: US 2005/0170206
Patent Document 20: US 2005/0170207
Non-patent Document 1: D. F. OBrien and M. A. Baldo et al "Improved energy transfer in electrophosphorescent devices" Vol. 74, No. 3, pp 442-444, Jan. 18, 1999
Non-patent Document 2: M. A. Baldo et al "Very high-efficiency green organic light-emitting devices based on electrophosphorescence" Applied Physics letters Vol. 75, No. 1, pp 4-6, Jul. 5, 1999
Non-patent Document 3: Chem. Rev. 2000, 100, p39
Non-patent Document 4: J. Am. Chem. Soc., 1991, 113, p361
Non-patent Document 5: Angnew. Chem. Int. Ed., 2002, 41, p1290
Non-patent Document 6: J. Am. Chem. Soc., 1999, 121, p2674
Non-patent Document 7: Organometallics, 1999, 18, p2370
Non-patent Document 8: Angnew. Chem. Int. Ed., 2002, 41, p1363
Non-patent Document 9: Angnew. Chem. Int. Ed., 2002, 41, p1745
Non-patent Document 10: Organometallics, 2000, 19, p3459
Non-patent Document 11: Tetrahedron Aymmetry, 2003, 14, p951
Non-patent Document 12: J. Organomet. Chem., 1982, 239, C26-C30
Non-patent Document 13: Chem. Commun., 2002, p2518

DISCLOSURE OF THE INVENTION

Problems to be Solved by the Invention

The present invention has been made with a view to solving the above-mentioned problems, and an object of the present invention is to provide an organic EL device having high luminous efficiency and a long emission lifetime, a blue light-emitting organic EL device having high luminous efficiency and a long emission lifetime, and a novel transition metal complex compound for realizing those organic electroluminescence devices.

Means for Solving the Problems

The inventors of the present invention have made extensive studies with a view to achieving the above object. As a result, the inventors have found that an organic EL device having high luminous efficiency and a long emission lifetime can be produced by using an iridium complex (transition metal complex compound) in which three ligands are crosslinked with a crosslinking group having a saturated cyclic structure or a saturated polycyclic structure in a tripod manner. In addition, the inventors have found that an organic EL device having high luminous efficiency and a long emission lifetime and emitting blue light can be produced by using an iridium complex having a metal carbene bond in a ligand. Thus, the inventors have completed the present invention.

That is, the present invention provides a transition metal complex compound represented by the following general formula (1):

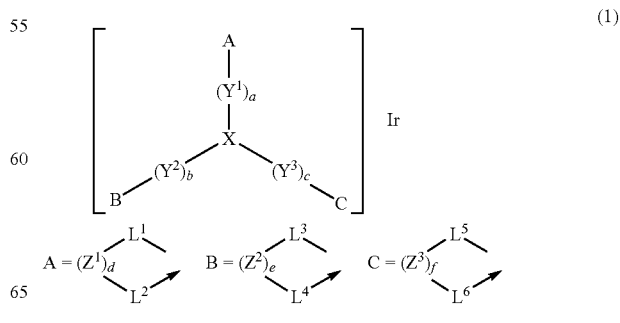

where:

A represents a crosslinking bidentate ligand group composed of $L^1\text{-}(Z^1)_d\text{-}L^2$, B represents a crosslinking bidentate ligand group composed of $L^3\text{-}(Z^2)_e\text{-}L^4$, and C represents a crosslinking bidentate ligand group composed of $L^5\text{-}(Z^3)_f\text{-}L^6$, $L^1$-, $L^3$-, and $L^5$- each represent a covalent bond to iridium (Ir) ($L^1$-Ir, $L^3$-Ir, and $L^5$-Ir), and $L^2\rightarrow$, $L^4\rightarrow$, and $L^6\rightarrow$ each represent a coordinate bond to Ir ($L^2\rightarrow$Ir, $L^4\rightarrow$Ir, and $L^6\rightarrow$Ir);

X represents a crosslinking group having 3 to 18 atoms and having a saturated cyclic structure or a saturated polycyclic structure, the crosslinking group being a trivalent residue of a compound constituted of an atom selected from the group consisting of a hydrogen atom, a carbon atom, a silicon atom, a nitrogen atom, a sulfur atom, an oxygen atom, a phosphorus atom, and a boron atom, and may have a substituent;

$Y^1$ represents a crosslinking group for bonding X and A, $Y^2$ represents a crosslinking group for bonding X and B, and $Y^3$ represents a crosslinking group for bonding X and C, $Y^1$ is bonded to $L^1$, $L^2$, or $Z^1$, $Y^2$ is bonded to $L^3$, $L^4$, or $Z^2$, and $Y^3$ is bonded to $L^5$, $L^6$, or $Z^3$, and $Y^1$, $Y^2$, and $Y^3$ each independently represent a divalent residue of a compound constituted of an atom selected from the group consisting of a hydrogen atom, a carbon atom, a silicon atom, a nitrogen atom, a sulfur atom, an oxygen atom, a phosphorus atom, and a boron atom, and each may have a substituent, a, b, and c each independently represent an integer of 0 to 10, and, when a, b, or c represents 2 or more, multiple $Y^1$'s, multiple $Y^2$'s, or multiple $Y^3$'s may be identical to or different from each other;

$Z^1$ represents a crosslinking group for bonding $L^1$ and $L^2$, $Z^2$ represents a crosslinking group for bonding $L^3$ and $L^4$, and $Z^3$ represents a crosslinking group for bonding $L^5$ and $L^6$, $Z^1$, $Z^2$, and $Z^3$ each independently represent a divalent residue of a compound constituted of an atom selected from the group consisting of a hydrogen atom, a carbon atom, a silicon atom, a nitrogen atom, a sulfur atom, an oxygen atom, a phosphorus atom, and a boron atom, and each may have a substituent, and when $Z^1$ is directly bonded to $Y^1$, when $Z^2$ is directly bonded to $Y^2$, or when $Z^3$ is directly bonded to $Y^3$, $Z^1$, $Z^2$, and $Z^3$ each represent a corresponding trivalent group, d, e, and f each independently represent an integer of 0 to 10, and, when d, e, or f represents 2 or more, multiple $Z^1$'s, multiple $Z^2$'s, or multiple $Z^3$'s may be identical to or different from each other;

$L^1$, $L^3$, and $L^5$ each independently represent a divalent aromatic hydrocarbon group which has 6 to 30 ring carbon atoms and which may have a substituent, a divalent heterocyclic group which has 3 to 30 ring atoms and which may have a substituent, a divalent carboxyl-containing group which has 1 to 30 carbon atoms and which may have a substituent, a divalent, amino group- or hydroxyl group-containing hydrocarbon group which may have a substituent, a cycloalkylene group which has 3 to 50 ring carbon atoms and which may have a substituent, an alkylene group which has 1 to 30 carbon atoms and which may have a substituent, an alkenylene group which has 2 to 30 carbon atoms and which may have a substituent, or an aralkylene group which has 7 to 40 carbon atoms and which may have a substituent, and when $L^1$ is directly bonded to $Y^1$, when $L^3$ is directly bonded to $Y^2$, or when $L^5$ is directly bonded to $Y^3$, $L^1$, $L^3$, and $L^5$ each represent a corresponding trivalent group; and $L^2$, $L^4$, and $L^6$ each independently represent a monovalent group which has carbene carbon and which may have a substituent, or a monovalent heterocyclic group which has 3 to 30 ring atoms and which may have a substituent, and when $L^2$ is directly bonded to $Y^1$, when $L^4$ is directly bonded to $Y^2$, or when $L^6$ is directly bonded to $Y^3$, $L^2$, $L^4$, and $L^6$ each represent a corresponding divalent group.

The present invention further provides an organic EL device which includes an organic thin film layer composed of one or multiple layers having at least a light emitting layer, the organic thin film layer being interposed between a cathode and an anode, in which at least one layer of the organic thin film layer contains the transition metal complex compound.

Effect of the Invention

The organic EL device using the transition metal complex compound of the present invention has high luminous efficiency and a long emission lifetime. In addition, the organic EL device using the transition metal complex compound having a metal carbene bond of the present invention emits blue light, and has high luminous efficiency and a long emission lifetime.

BEST MODE FOR CARRYING OUT THE INVENTION

Figure 1:
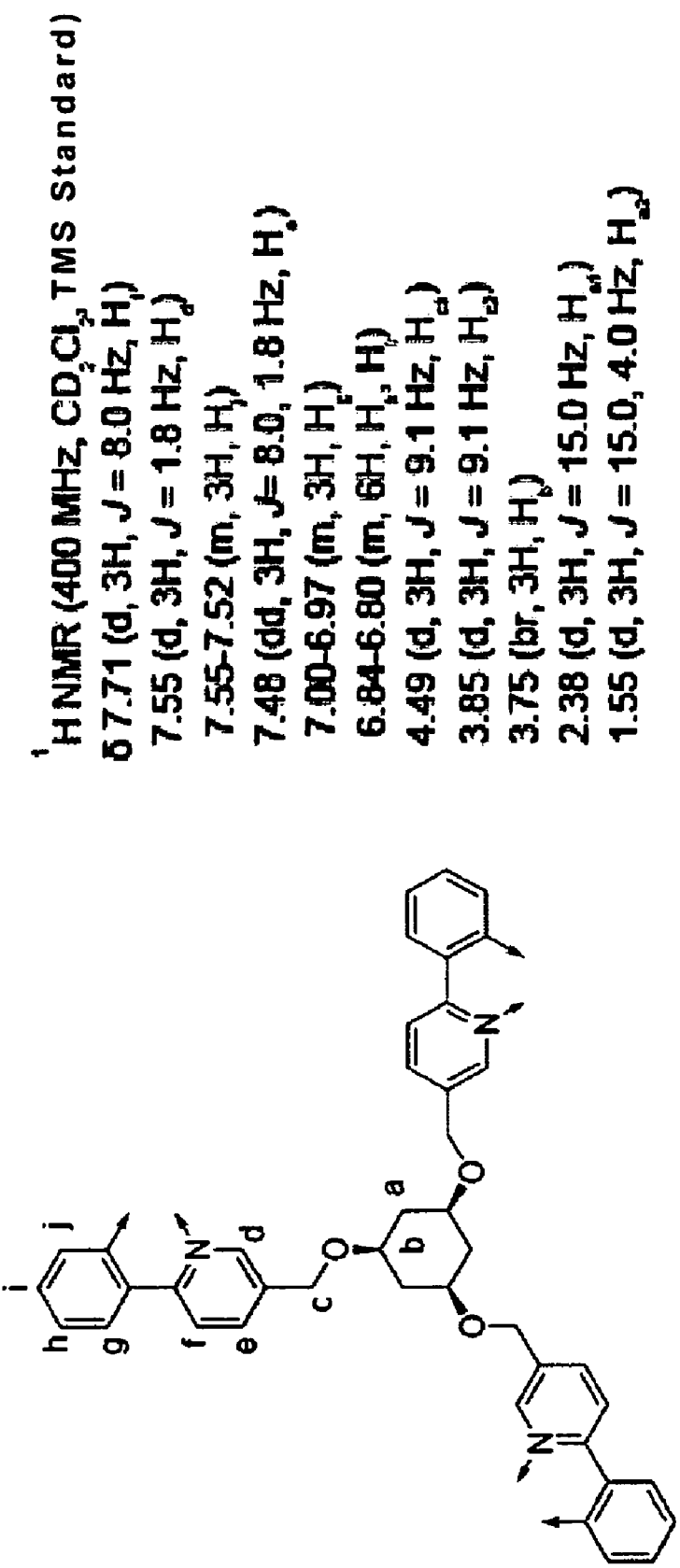
[FIG. 1] A view showing $^1$H-NMR spectrum data on Metal Complex Compound 8 obtained in Example 1.

A transition metal complex compound of the present invention is an iridium complex in which three ligands are crosslinked with a crosslinking group having a saturated cyclic structure or a saturated polycyclic structure in a tripod manner, and is preferably an iridium complex having metal carbene bonds in the three ligands.

The transition metal complex compound of the present invention as described above is represented by the following general formula (1).

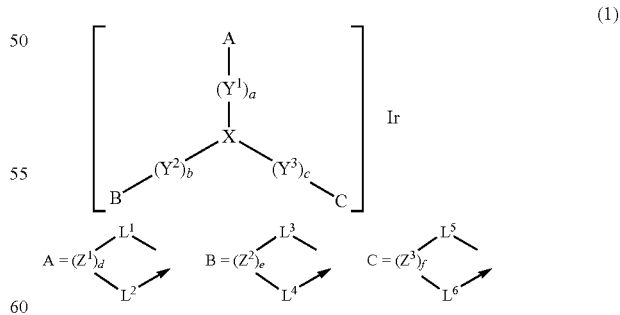

In the general formula (1), A represents a crosslinking bidentate ligand group composed of $L^1\text{-}(Z^1)_d\text{-}L^2$, B represents a crosslinking bidentate ligand group composed of $L^3\text{-}(Z^2)_e\text{-}L^4$, and C represents a crosslinking bidentate ligand group composed of $L^5\text{-}(Z^3)_f\text{-}L^6$, $L^1$-, $L^3$-, and $L^5$- each represent a covalent bond to iridium (Ir) ($L^1$-Ir, $L^3$-Ir, and $L^5$-Ir), and $L^2 \rightarrow$, $L^4 \rightarrow$, and $L^6 \rightarrow$ each represent a coordinate bond to Ir ($L^2 \rightarrow$Ir, $L^4 \rightarrow$Ir, and $L^6 \rightarrow$Ir).

In the general formula (1), X represents a crosslinking group having 3 to 18 atoms and having a saturated cyclic structure or a saturated polycyclic structure, the crosslinking group being a trivalent residue of a compound constituted of an atom selected from the group consisting of a hydrogen atom, a carbon atom, a silicon atom, a nitrogen atom, a sulfur atom, an oxygen atom, a phosphorus atom, and a boron atom, and may have a substituent. Of those, a cycloalkane residue is preferable.

Specific examples of such the saturated cyclic structure or the saturated polycyclic structure include a cyclopropane ring, a cyclobutane ring, a cyclopentane ring, a cyclohexane ring, a cycloheptane ring, a cyclooctane ring, a cyclononane ring, a cycloundecane ring, an adamantane ring, and a ring obtained by substituting at least one carbon atom constituting each of these rings by any one of a silicon atom, a nitrogen atom, a sulfur atom, an oxygen atom, a phosphorus atom, and a boron atom.

Of those, the crosslinking group X is preferably a cyclohexane residue, and is more preferably the following structure (2) (in a broken line).

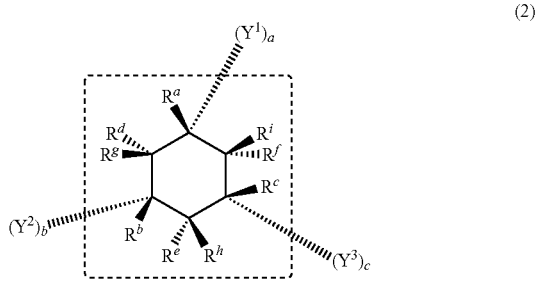

(2)

In the general formula (2), $R^a$ to $R^i$ each independently represent a hydrogen atom, an alkyl group which has 1 to 30 carbon atoms and which may have a substituent, a halogenated alkyl group which has 1 to 30 carbon atoms and which may have a substituent, an aromatic hydrocarbon group which has 6 to 30 ring carbon atoms and which may have a substituent, a cycloalkyl group which has 3 to 50 ring carbon atoms and which may have a substituent, an aralkyl group which has 7 to 40 carbon atoms and which may have a substituent, an alkenyl group which has 2 to 30 carbon atoms and which may have a substituent, a heterocyclic group which has 3 to 30 ring atoms and which may have a substituent, an alkoxy group which has 1 to 30 carbon atoms and which may have a substituent, an aryloxy group which has 6 to 30 ring carbon atoms and which may have a substituent, an alkylamino group which has 3 to 30 carbon atoms and which may have a substituent, an arylamino group which has 6 to 30 carbon atoms and which may have a substituent, an alkylsilyl group which has 3 to 30 carbon atoms and which may have a substituent, an arylsilyl group which has 6 to 30 carbon atoms and which may have a substituent, or a carboxyl-containing group which has 1 to 30 carbon atoms and which may have a substituent, and $R^a$ to $R^i$ may crosslink with one another, or may form polypod crosslinkage to bond 3 or more carbon atoms among 6 carbon atoms constituting cyclohexane.

For the alkyl group, an alkyl group having 1 to 10 carbon atoms is preferable, and examples thereof include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a hydroxymethyl group, a 1-hydroxyethyl group, a 2-hydroxyethyl group, a 2-hydoxyisobutyl group, a 1,2-dihydroxyehtyl group, a 1,3-dihydroxyisopropyl group, a 2,3-dihydroxy-t-butyl group, a 1,2,3-trihydroxypropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 1,2-dinitroethyl group, a 2,3-dinitro-t-butyl group, a 1,2,3-trinitropropyl group, a cyclopentyl group, a cyclohexyl group, a cyclooctyl group, and a 3,5-tetramethylcyclohexyl group.

Of those, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 1-pentylhexyl group, a 1-butylpentyl group, a 1-heptyloctyl group, a cyclohexyl group, a cyclooctyl group, and a 3,5-tetramethylcyclohexyl group are preferable.

For the halogenated alkyl group, a halogenated alkyl group having 1 to 10 carbon atoms is preferable, and examples thereof include a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a fluoromethyl group, a 1-fluoromethyl group, a 2-fluoromethyl group, a 2-fluoroisobutyl group, a 1,2-difluoroethyl group, a difluoromethyl group, a trifluoromethyl group, a pentafluoroethyl group, a perfluoroisopropyl group, a perfluorbutyl group, and a perfluorocyclohexyl group.

Of those, a fluoromethyl group, a trifluoromethyl group, a pentafluoroethyl group, a perfluoroisopropyl group, a perfluorbutyl group, and a perfluorocyclohexyl group are preferable.

For the aromatic hydrocarbon group, a hydrocarbon group having 6 to 18 ring carbon atoms is preferable, and examples thereof include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, 4"-t-butyl-p-terphenyl-4-yl group, an o-cumenyl group, an m-cumenyl group, a p-cumenyl group, a 2,3-xylylenyl group, a 3,4-xylylenyl group, a 2,5-xylylenyl group, a methytylenyl group, a mesitylenyl group, and a perfluorophenyl group.

Of those, a phenyl group, a 1-naphthyl group, a 2-naphthyl group, a 9-phenanthryl group, a 2-biphenylyl group, a 3-biphenylyl group, a 4-biphenylyl group, a p-tolyl group, and a 3,4-xylylenyl group are preferable.

Examples of the cycloalkyl group include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

For the aralkyl group, an aralkyl group having 7 to 18 carbon atoms is preferable, and examples thereof include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group. Of those, a benzyl group, a p-cyanobenzyl group, an m-cyanobenzyl group, an o-cyanobenzyl group, a 1-phenylethyl group, a 2-phenylethyl group, a 1-phenylisopropyl group, and a 2-phenylisopropyl group are preferable.

For the alkenyl group, an alkenyl group having 2 to 16 carbon atoms is preferable, and examples thereof include a vinyl group, an allyl group, a 1-butenyl group, a 2-butenyl group, a 3-butenyl group, a 1,3-butandienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, and a 3-phenyl-1-butenyl group. Of those, a styryl group, a 2,2-diphenylvinyl group, and a 1,2-diphenyl vinyl group are preferable.

For the heterocyclic group, a heterocyclic group having 3 to 18 ring atoms is preferable, and examples thereof include a 1-pyrrolyl group, a 2-pyrrolyl group, a 3-pyrrolyl group, a pyrazinyl group, a 2-pyridinyl group, a 1-imidazolyl group, a 2-imidazolyl group, a 1-pyrazolyl group, a 1-indolydinyl group, a 2-indolydinyl group, a 3-indolydinyl group, a 5-indolydinyl group, a 6-indolydinyl group, a 7-indolydinyl group, an 8-indolydinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a β-carbolin-1-yl group, a β-carbolin-3-yl group, a β-carbolin-4-yl group, a β-carbolin-5-yl group, a β-carbolin-6-yl group, a β-carbolin-7-yl group, a β-carbolin-8-yl group, a β-carbolin-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxadinyl group, a 2-phenoxadinyl group, a 3-phenoxadinyl group, a 4-phenoxadinyl group, a 10-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, a 4-t-butyl3-indolyl group, pyrrolidine, pyrazolidine, and piperalyzine.

Of those, a 2-pyridinyl group, a 1-indolydinyl group, a 2-indolydinyl group, a 3-indolydinyl group, a 5-indolydinyl group, a 6-indolydinyl group, a 7-indolydinyl group, an 8-indolydinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 1-carbazolyl group, a 2-carbazolyl group, a 3-carbazolyl group, a 4-carbazolyl group, and a 9-carbazolyl group are preferable.

The alkoxy group and the aryloxy group are each a group represented by —$OX^1$, and examples of $X^1$ include examples similar to those described for the alkyl group, the halogenated alkyl group, and the aryl group.

The alkylamino group and the arylamino group are each a group represented by —$NX^1X^2$, and examples of each of $X^1$ and $X^2$ include examples similar to those described for the alkyl group, the halogenated alkyl group, and the aryl group.

Examples of the carboxyl-containing group include methyl ester, ethyl ester, and butyl ester.

Examples of the alkylsilyl group include a trimethylsilyl group, a triethylsilyl group, a t-butyldimethylsilyl group, a vinyldimethylsilyl group, and a propyldimethylsilyl group.

Examples of the arylsilyl group include a triphenylsilyl group, a phenyldimethylsilyl group, and a t-butyldiphenylsilyl group.

In addition, examples of the ring structure formed as a result of the crosslinking of $R^a$ to $R^i$ described above include examples similar to those exemplified for the heterocyclic group and the aromatic hydrocarbon group.

It is particularly preferable that all of $R^a$ to $R^i$ in the general formula (2) each represent a hydrogen atom. In addition, specific examples of the general formula (2) are shown below.

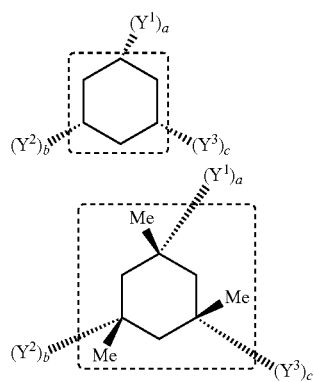

-continued

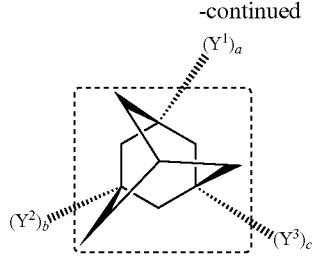

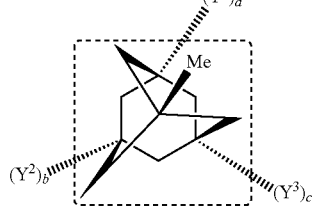

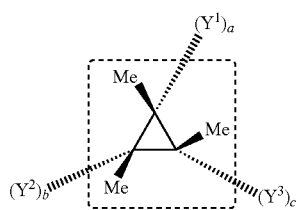

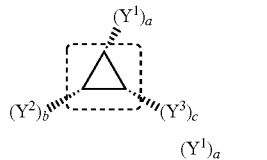

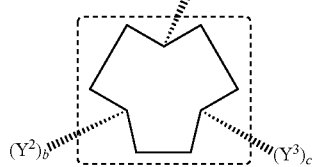

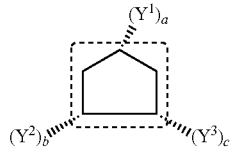

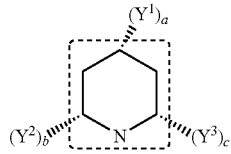

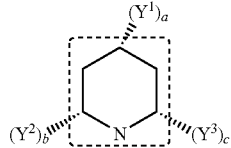

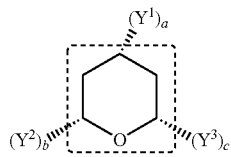

-continued

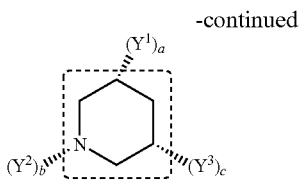

In the general formula (1), $Y^1$ represents a crosslinking group for bonding X and A, $Y^2$ represents a crosslinking group for bonding X and B, and $Y^3$ represents a crosslinking group for bonding X and C, $Y^1$ is bonded to $L^1$, $L^2$, or $Z^1$, $Y^2$ is bonded to $L^3$, $L^4$, or $Z^2$, and $Y^3$ is bonded to $L^5$, $L^6$, or $Z^3$, and $Y^1$, $Y^2$, and $Y^3$ each independently represent a divalent residue of a compound constituted of an atom selected from the group consisting of a hydrogen atom, a carbon atom, a silicon atom, a nitrogen atom, a sulfur atom, an oxygen atom, a phosphorus atom, and a boron atom, and each may have a substituent.

In the general formula (1), a, b, and c each independently represent an integer of 0 to 10, or preferably 0 to 3, and, when a, b, or c represents 2 or more, multiple $Y^1$'s, multiple $Y^2$'s, or multiple $Y^3$'s may be identical to or different from each other.

Specific examples of $Y^1$, $Y^2$, and $Y^3$ include —$CR^1R^2$—, —$SiR^1R^2$—, —$NR^1$—, —O—, —S—, —$PR^1$—, and —$BR^1$—. $R^1$ and $R^2$ each have the same meaning as that of each of $R^a$ to $R^i$ described above, and may be identical to or different from each other. In addition, $R^1$ and $R^2$ may crosslink with X, or may crosslink with each other. When a, b, and c each represent 2 or more, each of $Y^1$'s, $Y^2$'s, and $Y^3$'s can be arbitrarily selected from the group consisting of —$CR^1R^2$—, —$SiR^1R^2$—, —$NR^1$—, —O—, —S—, —$PR^1$—, and —$BR^1$— described above. In addition, in that case, $R^1$ and $R^2$ in each of $Y^1$'s, $Y^2$'s, and $Y^3$'s may crosslink with X, or may crosslink with each other.

Specific preferable structures of $Y^1$, $Y^2$, and $Y^3$ include-$CH_2$—, —$CMe_2$-, —CMeH—, —CEtH—, —O—, —S—, —$SiH_2$—, —$SiMe_2$-, —SiMeH—, —SiEtH—, —NH—, —NMe-, —NEt-, —PH—, —PMe-, —PEt-, —BH—, —BMe-, and —BEt- (where Me represents a methyl group and Et represents an ethyl group).

In the general formula (1), $Z^1$ represents a crosslinking group for bonding $L^1$ and $L^2$, $Z^2$ represents a crosslinking group for bonding $L^3$ and $L^4$, and $Z^3$ represents a crosslinking group for bonding $L^5$ and $L^6$, $Z^1$, $Z^2$, and $Z^3$ each independently represent a divalent residue of a compound constituted of an atom selected from the group consisting of a hydrogen atom, a carbon atom, a silicon atom, a nitrogen atom, a sulfur atom, an oxygen atom, a phosphorus atom, and a boron atom, and each may have a substituent, and when $Z^1$ is directly bonded to $Y^1$ when $Z^2$ is directly bonded to $Y^2$, or when $Z^3$ is directly bonded to $Y^3$, $Z^1$, $Z^2$, and $Z^3$ each represent a corresponding trivalent group.

In the general formula (1), d, e, and f each independently represent an integer of 0 to 10, or preferably 0 to 3, and, when d, e, or f represents 2 or more, multiple $Z^1$'s, multiple $Z^2$'s, or multiple $Z^3$'s may be identical to or different from each other.

Specific examples and specific preferable structures of $Z^1$, $Z^2$, and $Z^3$ include examples similar to those of $Y^1$, $Y^2$, and $Y^3$ described above and groups obtained by making the examples trivalent.

In the general formula (1), $L^1$, $L^3$, and $L^5$ each independently represent a divalent aromatic hydrocarbon group which has 6 to 30 ring carbon atoms and which may have a substituent, a divalent heterocyclic group which has 3 to 30 ring atoms and which may have a substituent, a divalent carboxyl-containing group which has 1 to 30 carbon atoms and which may have a substituent, a divalent, amino group- or hydroxyl group-containing hydrocarbon group which may have a substituent, a cycloalkylene group which has 3 to 50 ring carbon atoms and which may have a substituent, an alkylene group which has 1 to 30 carbon atoms and which may have a substituent, an alkenylene group which has 2 to 30 carbon atoms and which may have a substituent, or an aralkylene group which has 7 to 40 carbon atoms and which may have a substituent, and when $L^1$ is directly bonded to $Y^1$, when $L^3$ is directly bonded to $Y^2$, or when $L^5$ is directly bonded to $Y^3$, $L^1$, $L^3$, and $L^5$ each represent a corresponding trivalent group.

Examples of the divalent aromatic hydrocarbon group, the divalent heterocyclic group, the divalent carboxyl-containing group, the cycloalkylene group, the alkylene group, the alkenylene group, and the aralkylene group include those obtained by making examples of the aromatic hydrocarbon group, the heterocyclic group, the carboxyl-containing group, the cycloalkyl group, the alkyl group, the alkenyl group, and the aralkyl group described above for $R^a$ to $R^i$ divalent. Preferable examples of those groups include examples similar to those described above.

In addition, examples of the divalent, amino group- or hydroxyl group-containing hydrocarbon group include an amino group having a hydrocarbon group represented by each of $L^1$, $L^3$, and $L^5$ described above and a group obtained by substituting a hydrogen atom of the hydrocarbon group by a hydroxyl group.

In addition, $L^1$, $L^3$, and $L^5$ described above are each preferably an aromatic hydrocarbon group or a heterocyclic group. For example, they are each preferably any one of the structures shown below. Of those, a phenyl group and a substituted phenyl group are preferable. It should be noted that, in the following examples, Y represents an adjacent bonding group, that is, $L^2$, $L^4$, or $L^6$.

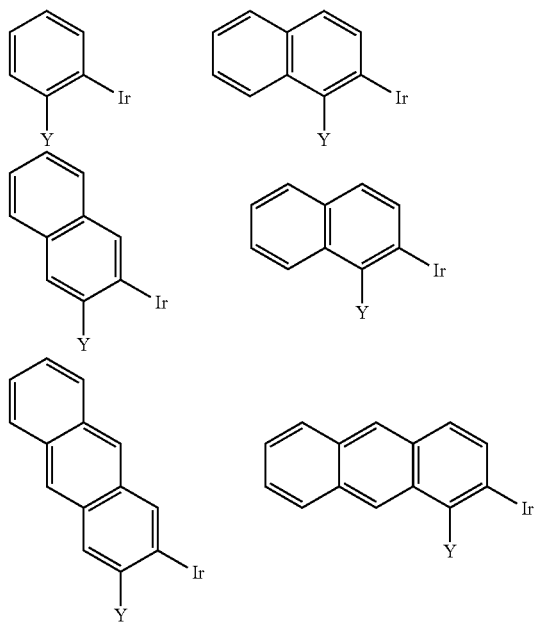

-continued
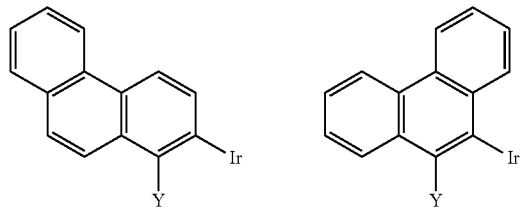
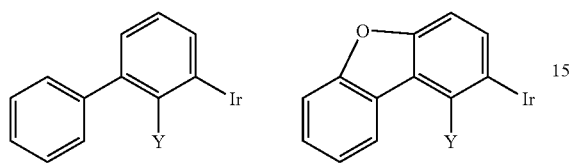
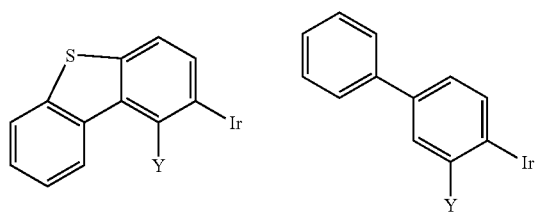
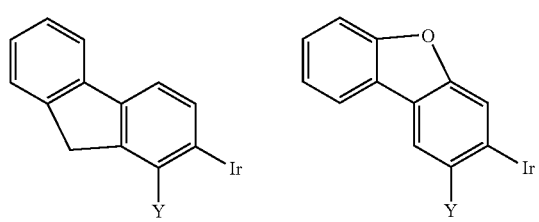
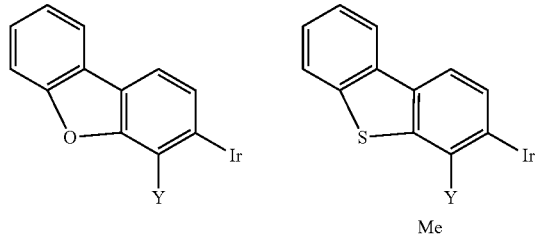
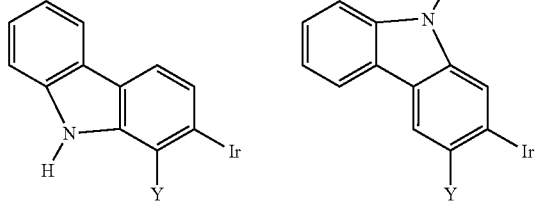
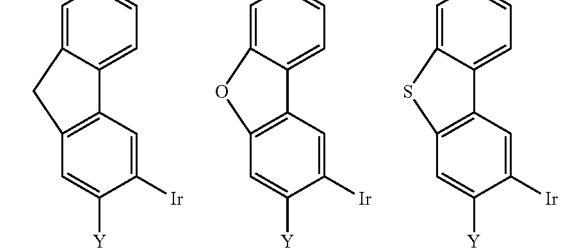
-continued
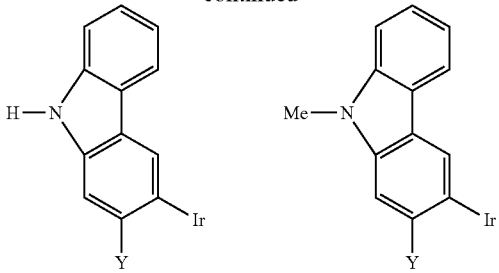
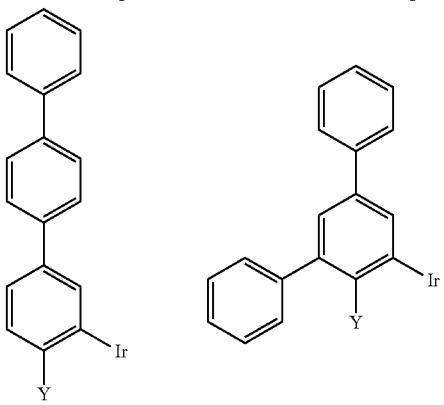
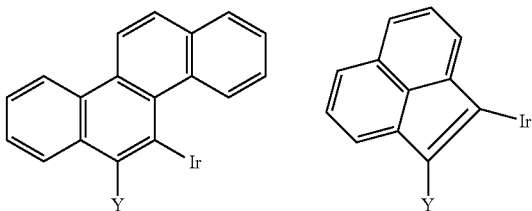
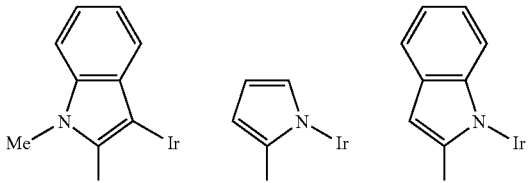
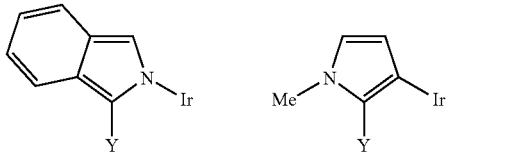
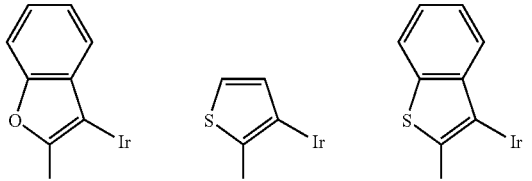
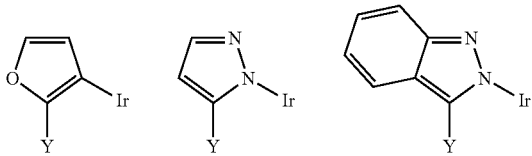

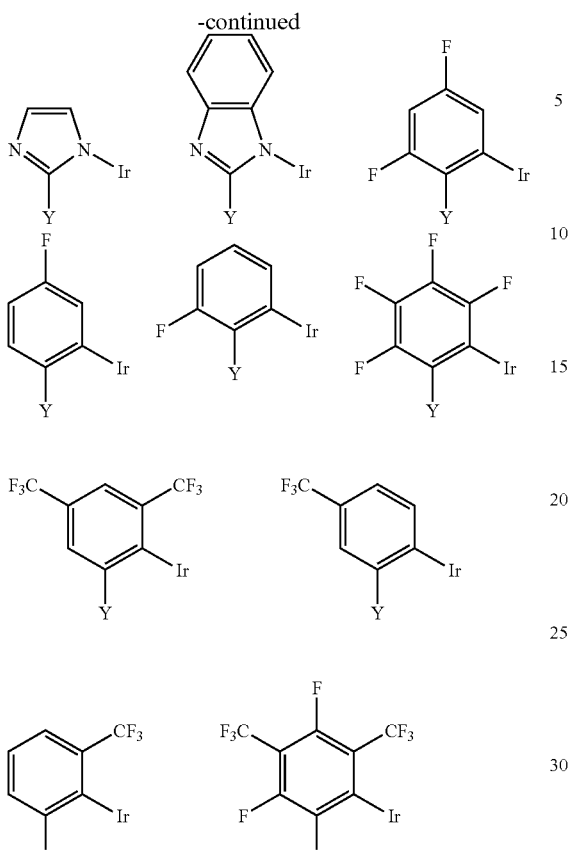

In the general formula (1), $L^2$, $L^4$, and $L^6$ each independently represent a monovalent group which has carbene carbon and which may have a substituent, or a monovalent heterocyclic group which has 3 to 30 ring atoms and which may have a substituent, and when $L^2$ is directly bonded to $Y^1$, when $L^4$ is directly bonded to $Y^2$, or when $L^6$ is directly bonded to $Y^3$, $L^2$, $L^4$, and $L^6$ each represent a corresponding divalent group. It is preferable that at least one of $L^2$, $L^4$, and $L^6$ represent a group having carbene carbon, and it is more preferable that $L^2$, $L^4$, and $L^6$ each represent a group having carbene carbon.

In addition, in ordinary cases, a monovalent group having carbene carbon is preferably one that forms stable carbene together with a metal. Specific examples of such the group include monovalent groups such as diarylcarbene, cyclic diaminocarbene, imidazol-2-ylidene, 1,2,4-triazol-3-ylidene, 1,3-thiazol-2-ylidene, non-cyclic diaminocarbene, non-cyclic aminooxycarbene, non-cyclic aminothiocarbene, cyclic diborylcarbene, non-cyclic diborylcarbene, phosphinosilylcarbene, phosphinophosphinocarbene, sulfenyltrifluoromethylcarbene, and sulfenylpentafluorothiocarbene groups (reference: Chem. Rev. 2000, 100, p 39).

Of those, imidazol-2-ylidene, 1,2,4-triazol-3-ylidene, and cyclic diaminocarbene groups are preferable, and imidazol-2-ylidene and 1,2,4-triazol-3-ylidene groups are more preferable. Specific structures of them are listed below. It should be noted that, in the following examples, an A ring represents an adjacent bonding group, that is, $L^1$, $L^3$, or $L^5$, and $R^j$ has the same meaning as that of each of $R^a$ to $R^i$ described above.

Further, specific preferable examples of the case where $L^2$, $L^4$, and $L^6$ each represent a group free of carbene carbon, that is, specific preferable examples of a heterocyclic group are listed below. In the following examples, carbon to be bonded to $L^1$, $L^3$, or $L^5$ is preferably adjacent to a hetero atom coordinated to iridium. Each of the following examples may be substituted.

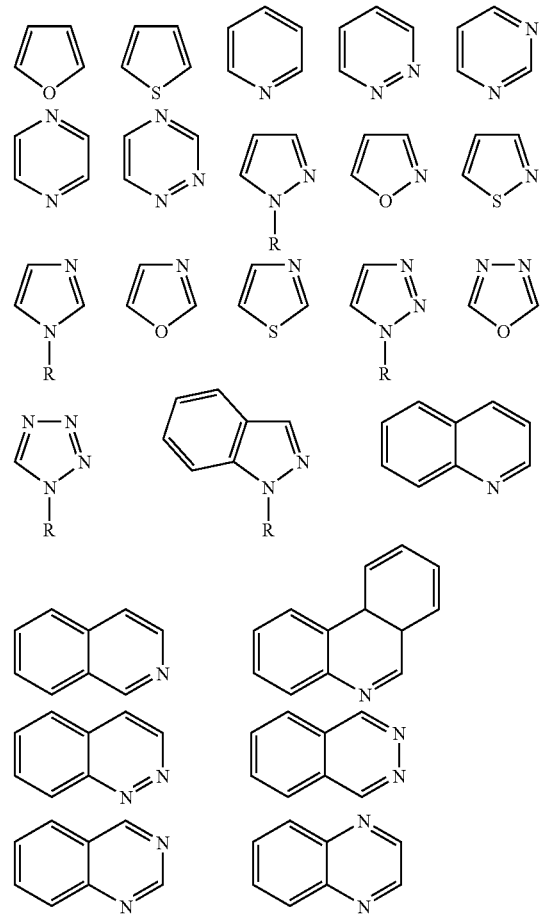

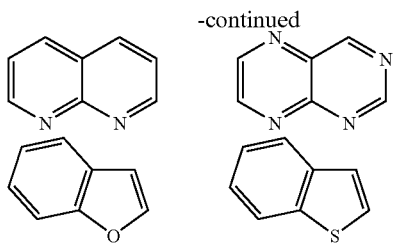

Examples of a substituent for each group in the general formula (1) include a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group, a halogen atom, a cyano group, a nitro group, a hydroxyl group, and a carboxyl group.

Of those, an alkyl group having 1 to 10 carbon atoms, a cycloalkyl group having 5 to 7 carbon atoms, and an alkoxy group having 1 to 10 carbon atoms are preferable, an alkyl group having 1 to 6 carbon atoms and a cycloalkyl group having 5 to 7 carbon atoms are more preferable, and a methyl group, an ethyl group, an n-propyl group, an isopropyl group, an n-butyl group, an sec-butyl group, a tert-butyl group, an n-pentyl group, an n-hexyl group, a cyclopentyl group, and a cyclohexyl group are particularly preferable.

Next, an example of a production process for a method of producing the transition metal complex compound represented by the general formula (1) of the present invention is shown below.

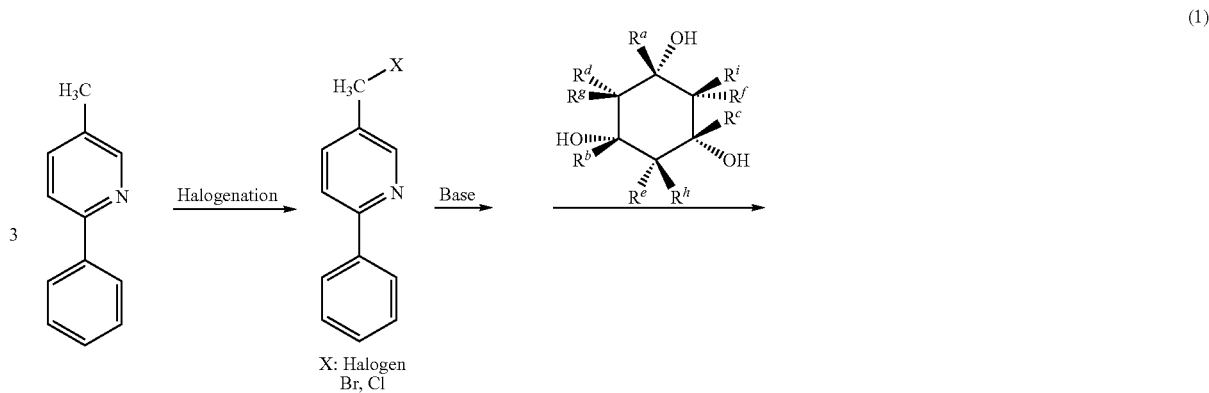

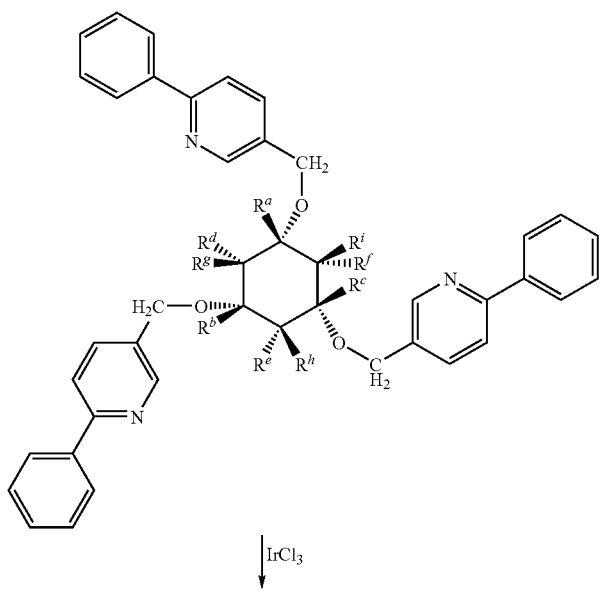

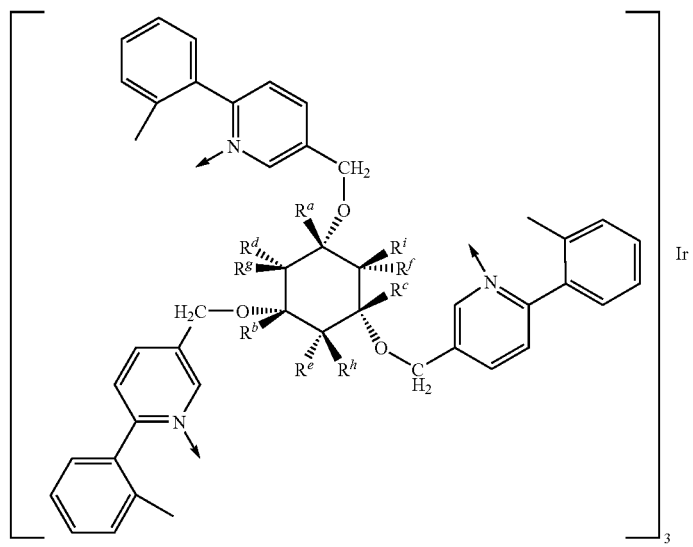
(2)
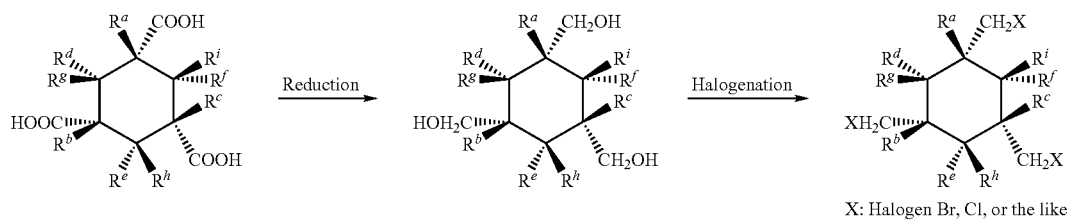
X: Halogen Br, Cl, or the like
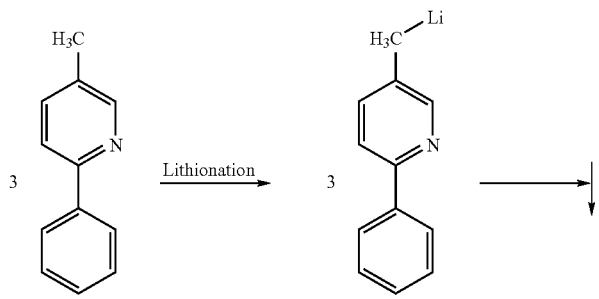
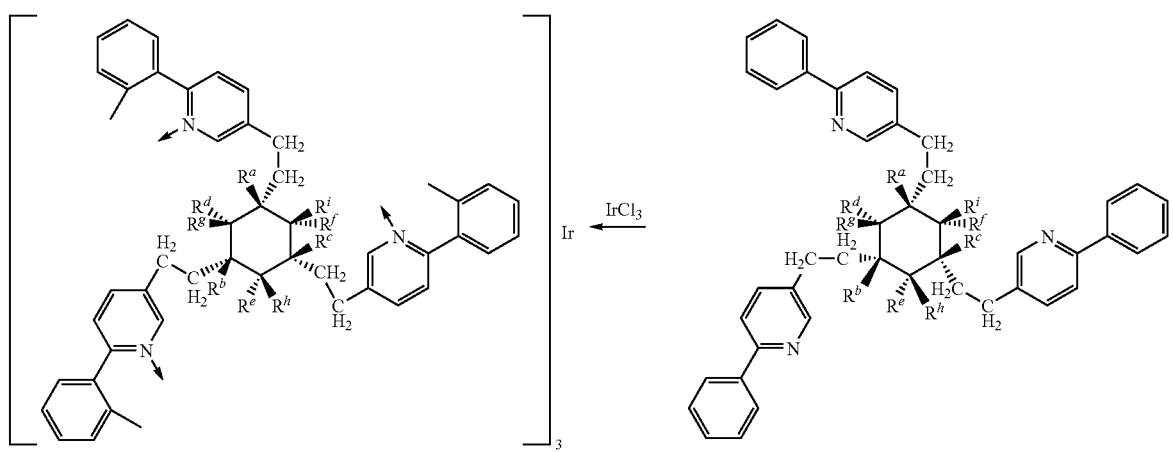

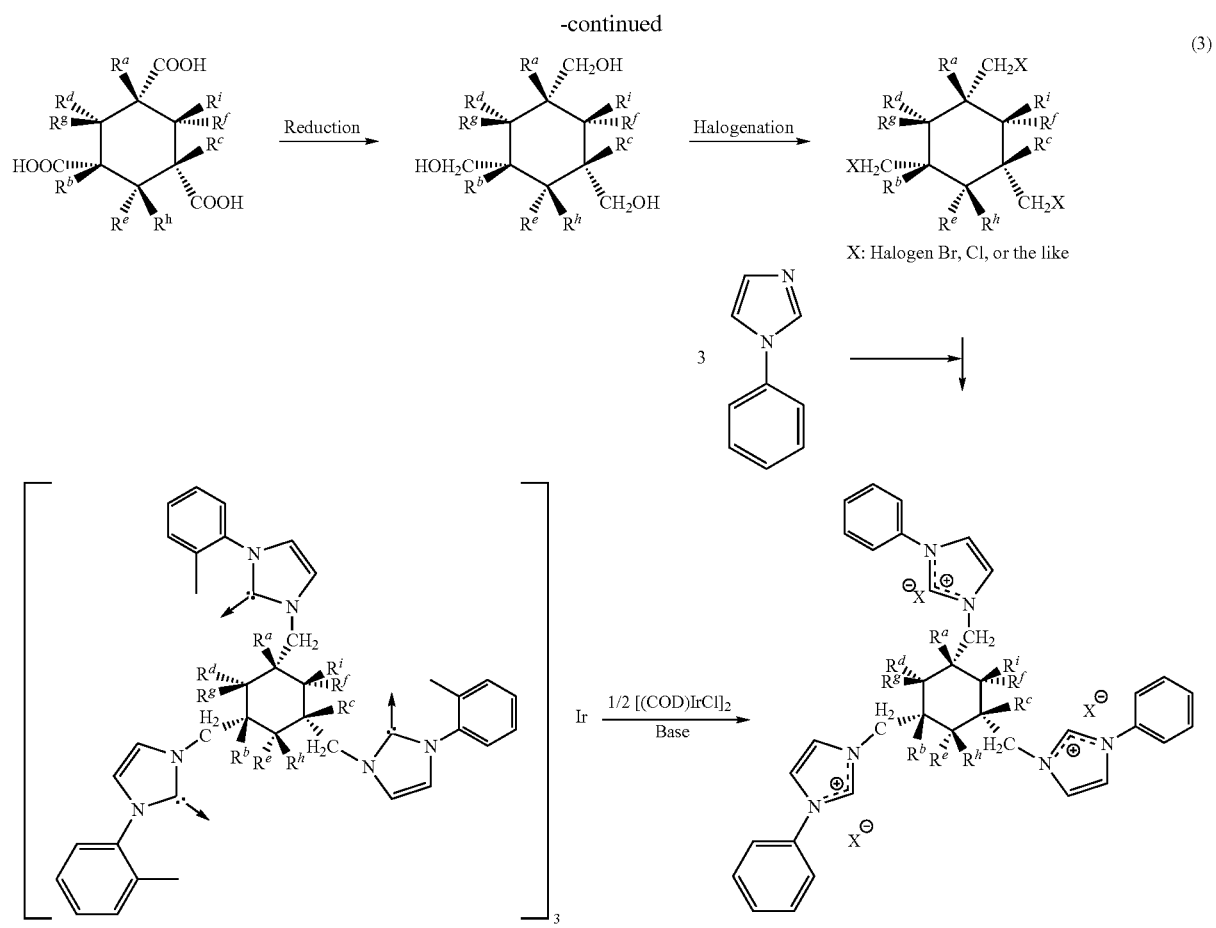

The organic EL device of the present invention is an organic EL device including an organic thin film layer composed of one or multiple layers having at least a light emitting layer, the organic thin film layer being interposed between a pair of electrodes consisting of a cathode and an anode, in which at least one layer of the organic thin film layer contains the transition metal complex compound represented by the general formula (1) of the present invention.

The content of the metal complex compound of the present invention in the organic thin film layer is typically 0.1 to 100 wt %, or preferably 1 to 30 wt % with respect to the mass of the entirety of the light emitting layer.

In the organic EL device of the present invention, the light emitting layer preferably contains the transition metal complex compound of the present invention as a light emitting material or as a dopant. In addition, the light emitting layer is typically formed into a thin film by vacuum deposition or application; a layer containing the transition metal complex compound of the present invention is preferably formed into a film by application because the application can simplify a production process.

In the organic EL device of the present invention, when the organic thin film layer is of a single-layer type, the organic thin film layer is a light emitting layer, and the light emitting layer contains the transition metal complex compound of the present invention. In addition, examples of a multilayer type organic EL device include: an organic EL device having a constitution of (anode/hole injecting layer (hole transporting layer)/light emitting layer/cathode); an organic EL device having a constitution of (anode/light emitting layer/electron injecting layer (electron transporting layer)/cathode); and an organic EL device having a constitution of (anode/hole injecting layer (hole transporting layer)/light emitting layer/electron injecting layer (electron transporting layer)/cathode).

The anode of the organic EL device of the present invention supplies a hole to the hole injecting layer, the hole transporting layer, the light emitting layer, or the like, and is effective when the anode has a work function of 4.5 eV or more. Examples of a material that can be used for the anode include a metal, an alloy, a metal oxide, an electroconductive compound, and a mixture of them. Specific examples of a material for the anode include: conductive metal oxides such as tin oxide, zinc oxide, indium oxide, and indium tin oxide (ITO); metals such as gold, silver, chromium, and nickel; a mixture or laminate of the conductive metal oxides and the metals; inorganic conductive substances such as copper iodide and copper sulfide; organic conductive materials such as polyaniline, polythiophene, and polypyrrole; and a laminate of the conductive substances or materials and ITO. Of those, the conductive metal oxides are preferable, and ITO is particularly preferably used in terms of, for example, productivity, high conductivity, and transparency. The thickness of the anode can be appropriately selected depending on the material.

The cathode of the organic EL device of the present invention supplies an electron to the electron injecting layer, the electron transporting layer, the light emitting layer, or the like. Examples of a material that can be used for the cathode include a metal, an alloy, a metal halide, a metal oxide, an electroconductive compound, and a mixture of them. Specific examples of a material for the cathode include: alkali metals (such as Li, Na, and K), and fluorides or oxides of the metals; alkali earth metals (such as Mg and Ca), and fluorides or oxides of the metals; gold; silver; lead; aluminum; a sodium-potassium alloy or a sodium-potassium mixed metal; a lithium-aluminum alloy or a lithium-aluminum mixed metal; a magnesium-silver alloy or a magnesium-silver mixed metal; and rare earth metals such as indium and ytterbium. Of those, aluminum, the lithium-aluminum alloy or the lithium-aluminum mixed metal, the magnesium-silver alloy or the magnesium-silver mixed metal, or the like is preferable. The cathode may be structured by a single layer containing any one of the materials, or may be structured by laminating layers each containing any one of the materials. For example, the cathode is preferably of a laminate structure of aluminum/lithium fluoride or of aluminum/lithium oxide. The thickness of the cathode can be appropriately selected depending on the material.

Each of the hole injecting layer and hole transporting layer of the organic EL device of the present invention only needs to have any one of a function of injecting a hole from the anode, a function of transporting a hole, and a function of blocking an electron injected from the cathode. Specific examples of a material for each of the layers include: a carbazole derivative; a triazole derivative; an oxazole derivative; an oxadiazole derivative; an imidazole derivative; a polyarylalkane derivative; a pyrazoline derivative; a pyrazolone derivative; a phenylenediamine derivative; an arylamine derivative; an amino-substituted chalcone derivative; a styrylanthracene derivative; a fluorenone derivative; a hydrazone derivative; a stilbene derivative; a silazane derivative; an aromatic tertiary amine compound; a styrylamine compound; an aromatic dimethylidyne-based compound; a porphyrin-based compound; a polysilane-based compound; a poly(N-vinylcarbazole) derivative; an aniline-based copolymer; a conductive, high-molecular-weight oligomer such as a thiophene oligomer or polythiophene; an organic silane derivative; and the transition metal complex compound of the present invention. In addition, each of the hole injecting layer and the hole transporting layer may be of a single-layered structure composed of one or two or more of the materials, or may be of a multi-layered structure composed of multiple layers identical to or different from each other in composition.

Each of the electron injecting layer and electron transporting layer of the organic EL device of the present invention only needs to have any one of a function of injecting an electron from the cathode, a function of transporting an electron, and a function of blocking a hole injected from the anode. Specific examples of a material for each of the layers include: a triazole derivative; an oxazole derivative; an oxadiazole derivative; an imidazole derivative; a fluorenone derivative; an anthraquinodimethane derivative; an anthrone derivative; a diphenylquinone derivative; a thiopyranedioxide derivative; a carbodiimide derivative; a fluorenylidenemethane derivative; a distyrylpyrazine derivative; aromatic tetracarboxylic anhydrides such as naphthalene and perylene; various metal complexes typified by metal complexes of a phthalocyanine derivative and an 8-quinolinol derivative, a metal phthalocyanine, and a metal complex using benzoxazole or benzothiazole as a ligand; an organic silane derivative; and the transition metal complex compound of the present invention. In addition, each of the electron injecting layer and the electron transporting layer may be of a single-layered structure composed of one or two or more of the materials, or may be of a multi-layered structure composed of multiple layers identical to or different from each other in composition.

Further, examples of an electron transporting material for use in each of the electron injecting layer and the electron transporting layer include the following compounds.

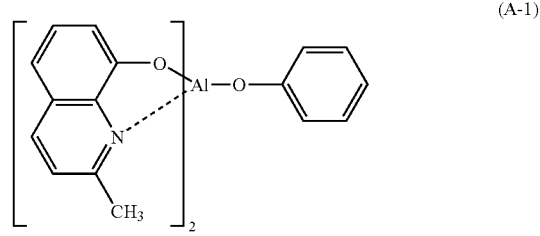

(A-1)

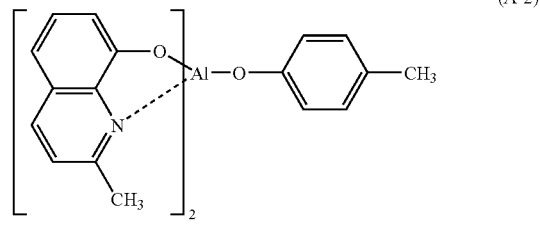

(A-2)

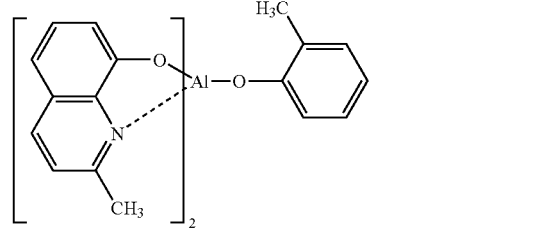

(A-3)

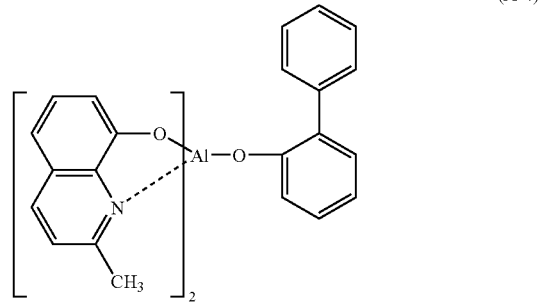

(A-4)

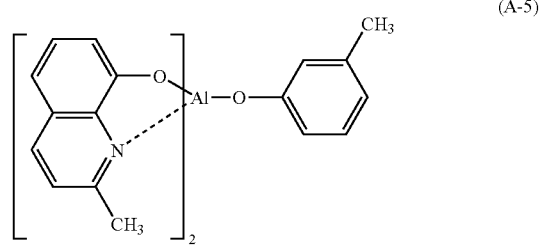

(A-5)

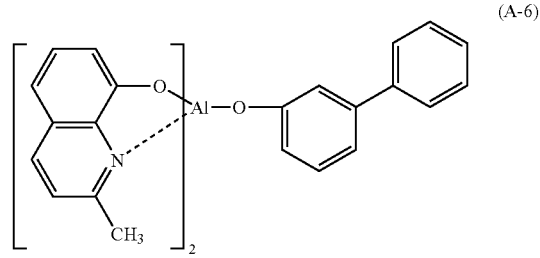

(A-6)

-continued
(A-7)
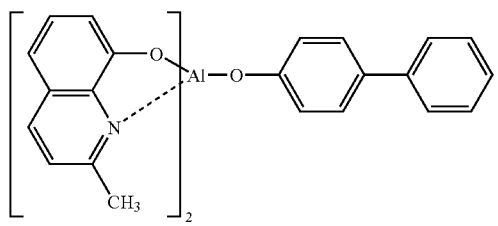
(A-8)
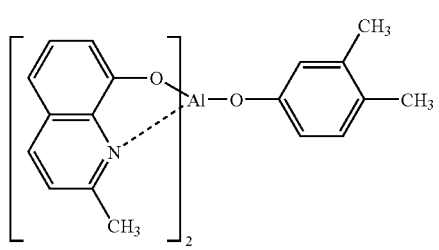
(A-9)
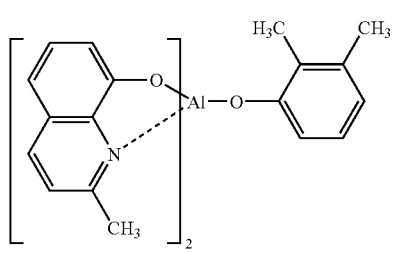
(A-10)
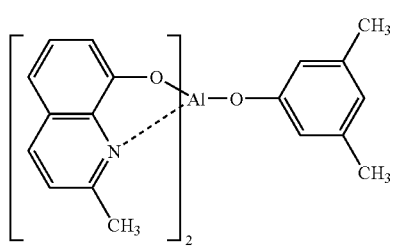
(A-11)
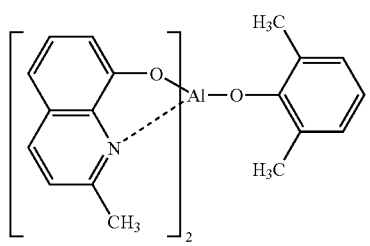
(A-12)
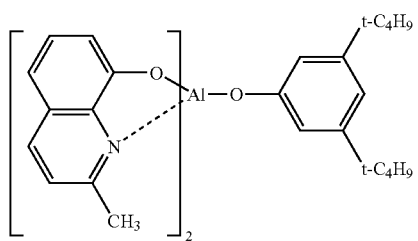
-continued
(A-13)
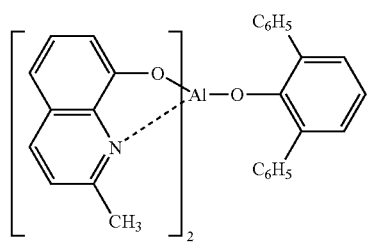
(A-14)
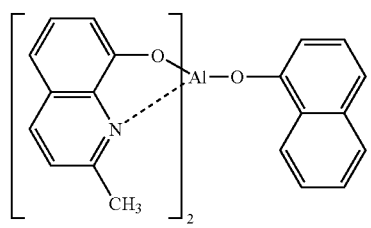
(A-15)
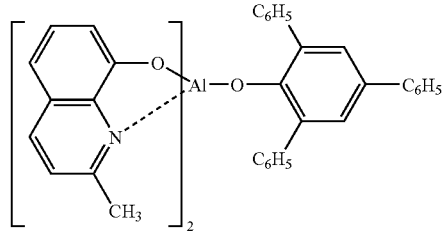
(A-16)
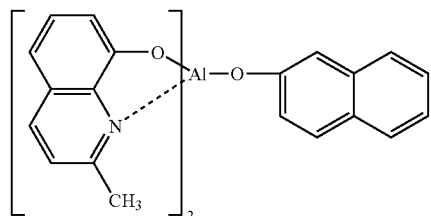
(A-17)
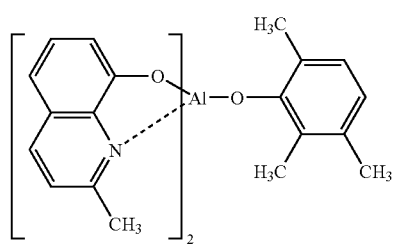
(A-18)
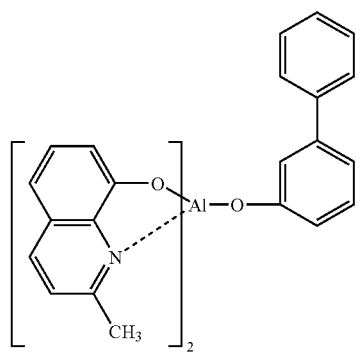

(A-19)
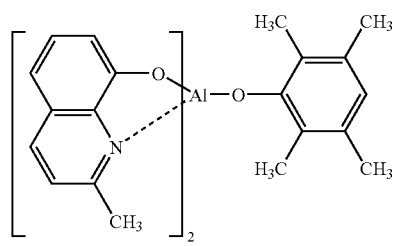
(A-20)
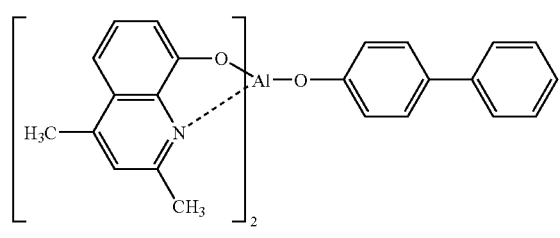
(A-21)
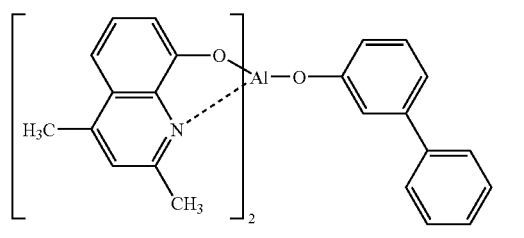
(A-22)
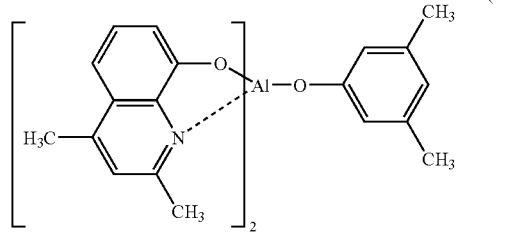
(A-23)
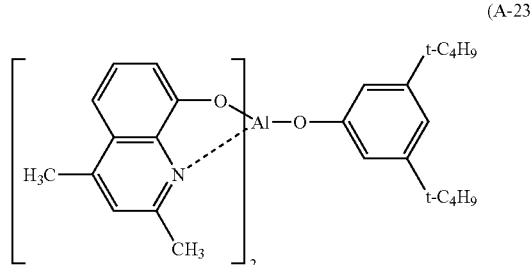
(A-24)
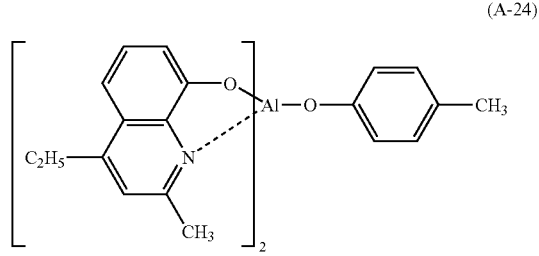
(A-25)
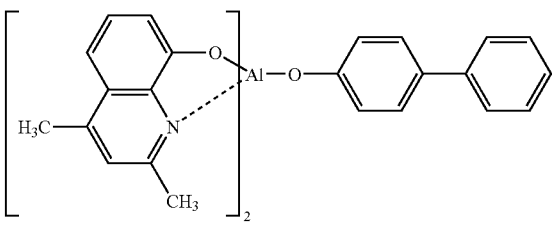
(A-26)
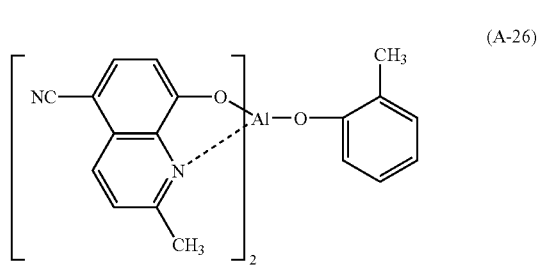
(A-27)
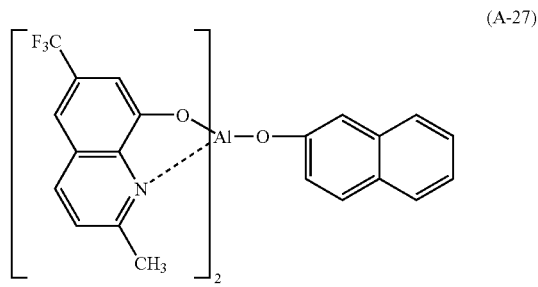
(A-28)
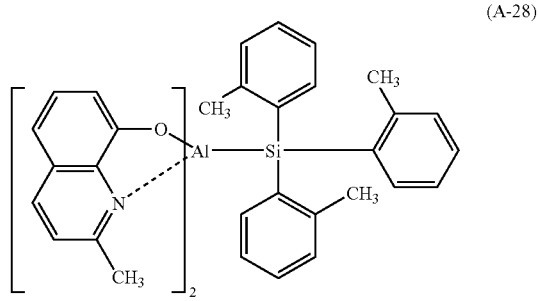
(A-29)
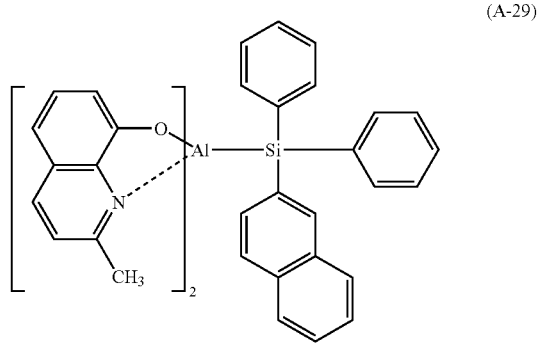

-continued

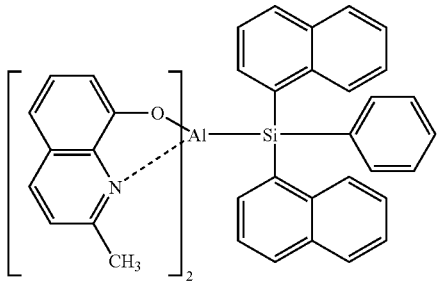 (A-30)

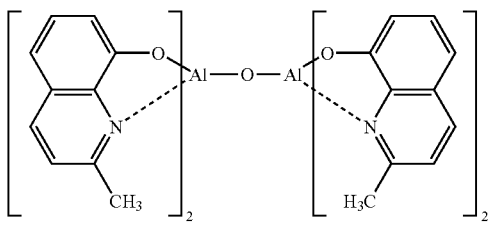 (A-31)

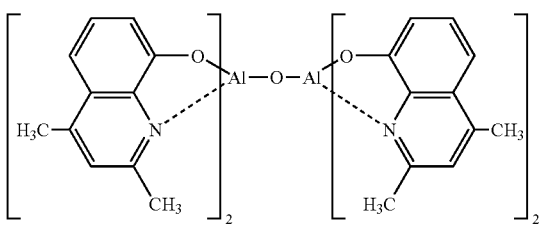 (A-32)

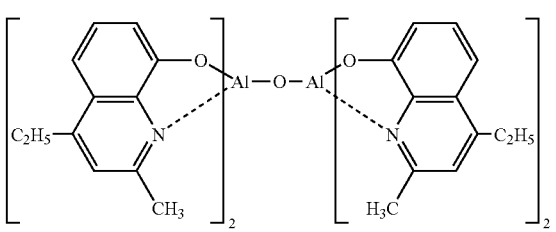 (A-33)

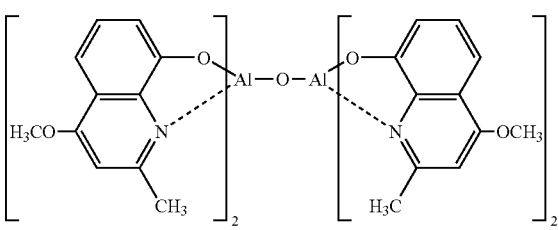 (A-34)

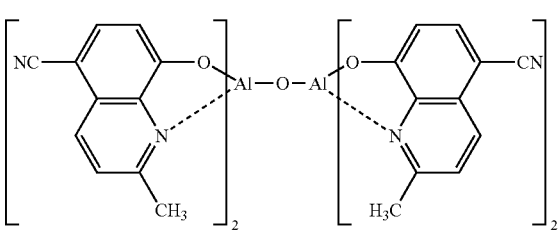 (A-35)

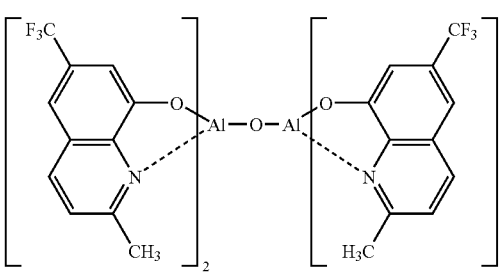 (A-36)

In the organic EL device of the present invention, at least one of the electron injecting layer and the electron transporting layer preferably contains a n-electron-deficient, nitrogen-containing heterocyclic derivative as a main component.

Preferable examples of the n-electron-deficient, nitrogen-containing heterocyclic derivative include: a derivative of a nitrogen-containing five-membered ring selected from the group consisting of a benzimidazole ring, a benztriazole ring, a pyridinoimidazole ring, a pyrimidinoimidazole ring, and a pyridazinoimidazole ring; and a nitrogen-containing six-membered ring derivative constituted of a pyridine ring, a pyrimidine ring, a pyrazine ring, or a triazine ring. A preferable example of the structure of the nitrogen-containing five-membered ring derivative is one represented by the following general formula B-I. Preferable examples of the structure of the nitrogen-containing six-membered ring derivative include those represented by the following general formulae C-I, C-II, C-III, C-IV, C-V, and C-VI. Of those, the structures represented by the general formulae C-I and C-II are particularly preferable.

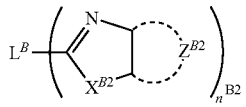 (B-I)

In the general formula (B-I), $L^B$ represents a linking group having a functionality of two or greater. The linking group is preferably formed of carbon, silicon, nitrogen, boron, oxygen, sulfur, a metal, a metal ion, or the like, more preferably a carbon atom, a nitrogen atom, a silicon atom, a boron atom, an oxygen atom, a sulfur atom, an aromatic hydrocarbon ring, a heteroaromatic ring, and still more preferably a carbon atom, a silicon atom, an aromatic hydrocarbon ring, or a heteroaromatic ring.

$L^B$ may have a substituent. For the substituent, an alkyl group, an alkenyl group, an alkynyl group, an aromatic hydrocarbon group, an amino group, an alkoxyl group, an aryloxyl group, an acyl group, an alkoxycarbonyl group, an aryloxycarbonyl group, an acyloxyl group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, and a heteroaromatic group are preferable. An alkyl group, an aryl group, an alkoxyl group, an aryloxyl group, a halogen atom, a cyano group, and a heteroaromatic group are more preferable. An alkyl group, an aryl group, an alkoxyl group, an aryloxyl group, and a heteroaromatic group are still more preferable, and an alkyl group, an aryl group, an alkoxyl group, and a heteroaromatic group are particularly preferable.

Specific examples of the linking group represented by $L^B$ include the following.

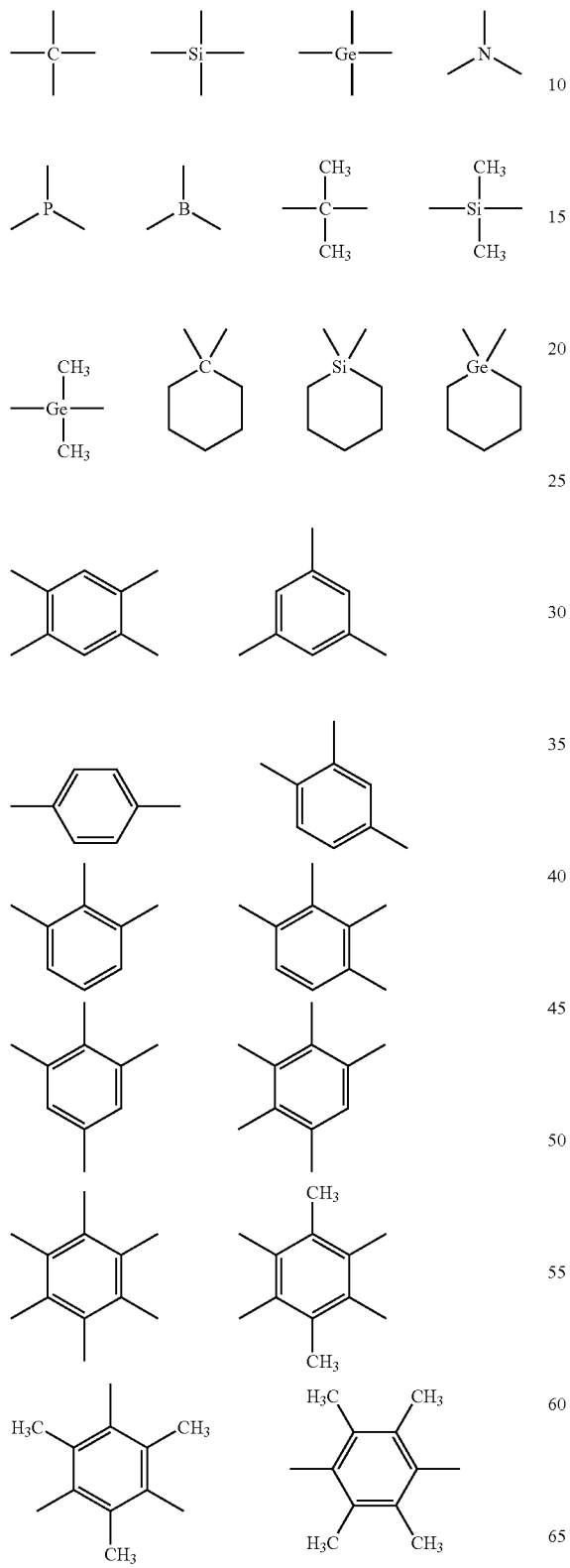

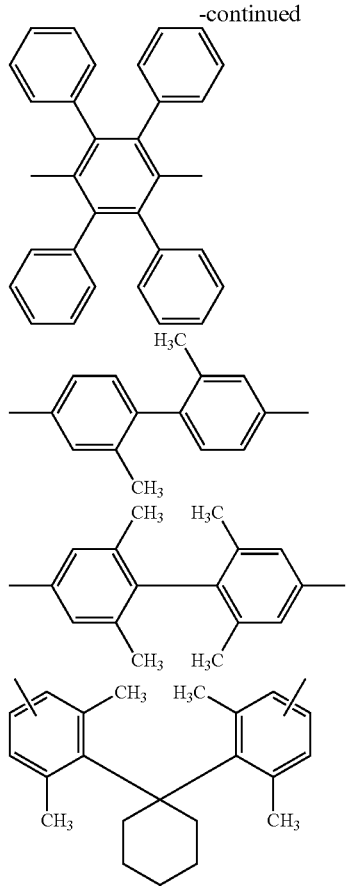

In the general formula (B-I), $X^{B2}$ represents —O—, —S— =N—$R^{B2}$. $R^{B2}$ represents a hydrogen atom, an aliphatic hydrocarbon group, an aryl group, or a heterocyclic group.

The aliphatic hydrocarbon group represented by $R^{B2}$ is a linear, branched or cyclic alkyl group (an alkyl group preferably having 1 to 20 carbon atoms, more preferably 1 to 12 carbon atoms, or particularly preferably 1 to 8 carbon atoms, such as a methyl group, an ethyl group, an iso-propyl group, a tert-butyl group, an n-octyl group, an n-decyl group, an n-hexadecyl group, a cyclopropyl group, a cyclopentyl group, or a cyclohexyl group), an alkenyl group (an alkenyl group preferably having 2 to 20 carbon atoms, more preferably 2 to 12 carbon atoms, or particularly preferably 2 to 8 carbon atoms, such as a vinyl group, an allyl group, a 2-butenyl group, or a 3-pentenyl group), or an alkynyl group (an alkynyl group preferably having 2 to 20 carbon atoms, more preferably 2 to 12 carbon atoms, or particularly preferably 2 to 8 carbon atoms, such as a propargyl group or a 3-pentynyl group). Of those, an alkyl group is more preferable.

The aryl group represented by $R^{B2}$ is a group having a single ring or a condensed ring. The aryl group preferably has 6 to 30 carbon atoms, more preferably has 6 to 20 carbon atoms, and still more preferably has 6 to 12 carbon atoms, and examples thereof include a phenyl group, a 2-methylphenyl group, a 3-methylphenyl group, a 4-methylphenyl group, a 2-methoxyphenyl group, a 3-trifluoromethylphenyl group, a pentafluorophenyl group, a 1-naphthyl group, and a 2-naphthyl group.

The heterocyclic group represented by $R^{B2}$ has a single ring or a condensed ring (a heterocyclic group preferably having 1 to 20 carbon atoms, more preferably 1 to 12 carbon atoms, and still more preferably 2 to 10 carbon atoms), and is preferably a heteroaromatic group having at least one of a nitrogen atom, an oxygen atom, a sulfur atom, and a selenium atom. Examples of the heterocyclic group include pyrrolidine, piperidine, piperazine, morpholine, thiophene, selenophene, furan, pyrrol, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthylidine, quinoxaline, quinazoline, cinnoline, puteridine, acridine, phenanthroline, phenazine, tetrazole, benzoimidazole, benzoxazole, benzothiazole, benzotriazole, tetrazaindene, carbazole, and azepine. Of those, furan, thiophene, pyridine, pyrazine, pyrimidine, pyridazine, triazine, quinoline, phthalazine, naphthylidine, quinoxaline, and quinazoline are preferable, furan, thiophene, pyridine, and quinoline are more preferable, and quinoline is still more preferable.

The aliphatic hydrocarbon group, the aryl group, and the heterocyclic group each of which is represented by $R^{B2}$ may have a substituent, and examples of the substituent include the same substituents as those in the case of $L^B$.

Examples of $R^{B2}$ preferably include an alkyl group, an aryl group, and a heteroaromatic group, more preferably an aryl group and a heteroaromatic group, and still more preferably an aryl group.

$X^{B2}$ preferably represents —O— or =N—$R^{B2}$, more preferably represents =N—$R^{B2}$, or particularly preferably represents =N—$Ar^{B2}$ (where $Ar^{B2}$ represents an aryl group (aryl group having preferably 6 to 30 carbon atoms, more preferably 6 to 20 carbon atoms, or still more preferably 6 to 12 carbon atoms) or a heteroaromatic group (heteroaromatic group having preferably 1 to 20 carbon atoms, more preferably 1 to 12 carbon atoms, or still more preferably 2 to 10 carbon atoms), or preferably represents an aryl group).

$Z^{B2}$ represents a group of atoms necessary for forming an aromatic ring. The aromatic ring formed with the group of atoms represented by $Z^{B2}$ may be any one of an aromatic hydrocarbon ring and a heteroaromatic ring. Specific examples of the aromatic ring include abenzene ring, a pyridine ring, a pyrazine ring, a pyrimidine ring, a pyridazine ring, a triazine ring, a pyrrol ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrazole ring. Of those rings, a benzene ring, a pyridine ring, a pyrazine ring, a pyrimidine ring, and a pyridazine ring are preferable, and a benzene ring, a pyridine ring, and a pyrazine ring are more preferable. A benzene ring and a pyridine ring are still more preferable, and a pyridine ring is particularly preferable. The aromatic ring formed with the group of atoms represented by $Z^{B2}$ may form a condensed ring with another ring, and may have a substituent. Preferable examples of the substituent include an alkyl group, an alkenyl group, an alkynyl group, an aryl group, an amino group, an alkoxyl group, an aryloxyl group, an acyl group, an alkoxycarbonyl group, an aryloxycarbonyl group, an acyloxyl group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, and a heterocyclic group. An alkyl group, an aryl group, an alkoxyl group, an aryloxyl group, a halogen atom, a cyano group, and a heterocyclic group are more preferable. An alkyl group, an aryl group, an alkoxyl group, an aryloxyl group, and a heteroaromatic group are still more preferable, and an alkyl group, an aryl group, an alkoxyl group, and a heteroaromatic group are particularly preferable.

$n^{B2}$ represents an integer of 1 to 4 and preferably 2 to 3.

Of the compounds represented by the general formula (B-I), compounds represented by the following general formula (B-II) are more preferable.

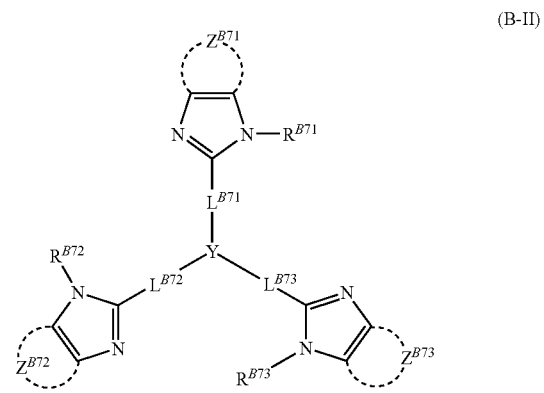

(B-II)

In the general formula (B-II), $R^{B71}$, $R^{B72}$, and $R^{B73}$ each represent the same atom or group as those represented by $R^{B2}$ in the general formula (B-I). Preferable examples of the group represented by $R^{B7}$, $R^{B72}$, and $R^{B73}$ include the group described as the preferable examples of the groups represented by $R^{B2}$ in the general formula (B-I).

$Z^{B71}$, $Z^{B72}$, and $Z^{B73}$ each represent the same groups as those in the case of $Z^{B2}$ in the general formula (B-I). Preferable examples of the group represented by $Z^{B71}$, $Z^{B72}$, and $Z^{B73}$ include the group described as the preferable examples of the group represented by $Z^{B2}$ in the general formula (B-I).

$L^{B71}$, $L^{B72}$, and $L^{B73}$ each represent a linking group, examples of which include the linking group described as the examples of the divalent linking group represented by $L^B$ in the general formula (B-I). It is preferable that the linking group be a single bond, a divalent aromatic hydrocarbon cyclic group, a divalent heteroaromatic group, or a combination of those groups, and more preferably a single bond. The linking group represented by $L^{B71}$, $L^{B72}$, and $L^{B73}$ may have a substituent. Examples of the substituent include the same substituents as those in the case of LB in the general formula (B-I).

Y represents a nitrogen atom, a 1,3,5-benzentriyl group, or a 2,4,6-triazintriyl group. 1,3,5-benzentriyl group may have a substituent at 2,4,6-positions. Examples of the substituent include an alkyl group, an aromatic hydrocarbon cyclic group, and a halogen atom.

Specific examples of the five-membered nitrogen-containing ring derivative represented by the general formula (B-I) and (B-II) are shown in the following. However, the five-membered nitrogen-containing ring derivative is not limited to the compounds shown as the examples.

-continued
(B-1) 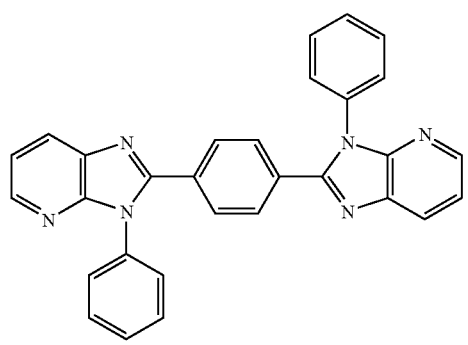
(B-5) 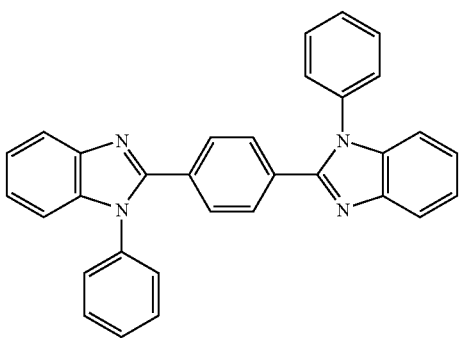
(B-2) 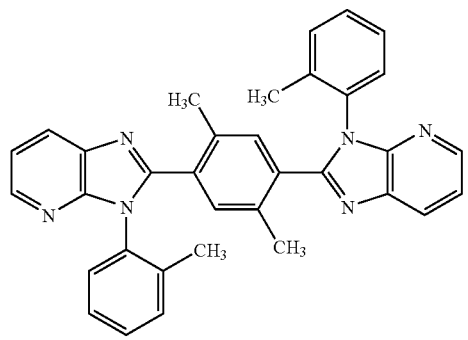
(B-6) 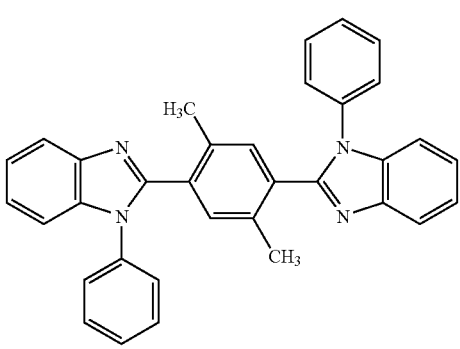
(B-3) 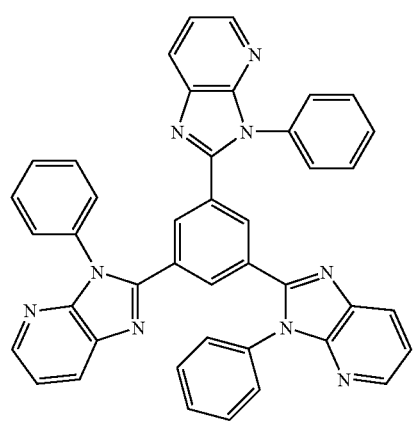
(B-7) 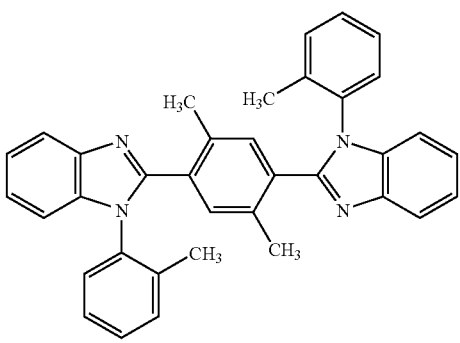
(B-4)
(B-8)

-continued
(B-9)
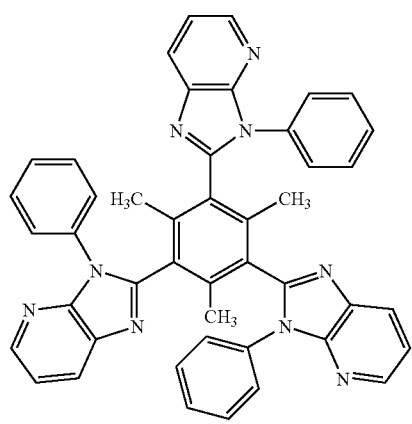
(B-12)
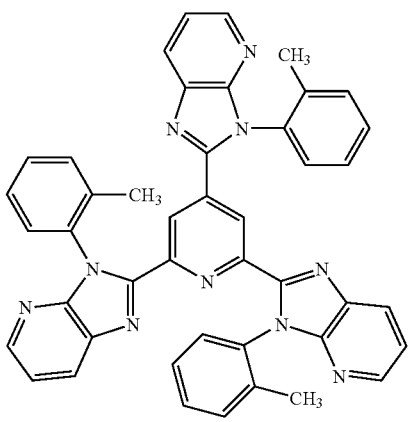
(B-10)
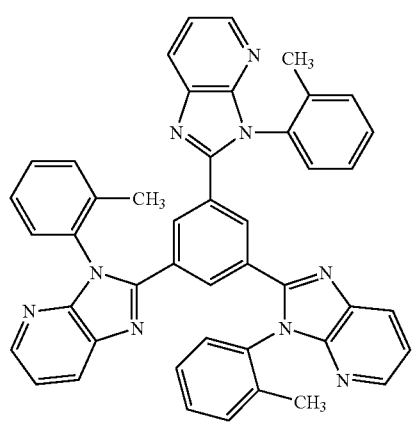
(B-13)
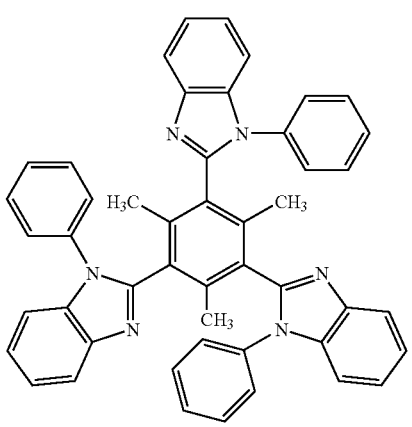
(B-11)
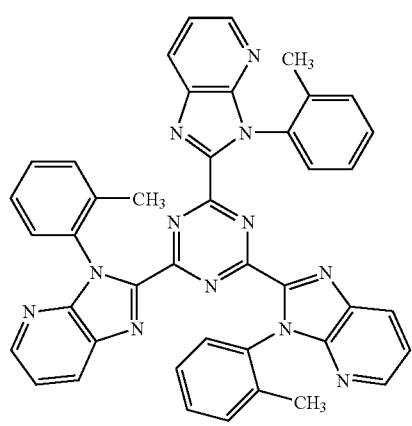
(B-14)
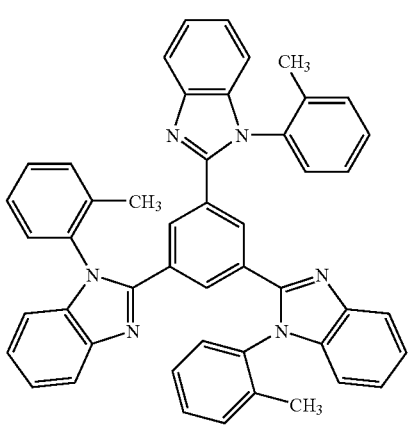

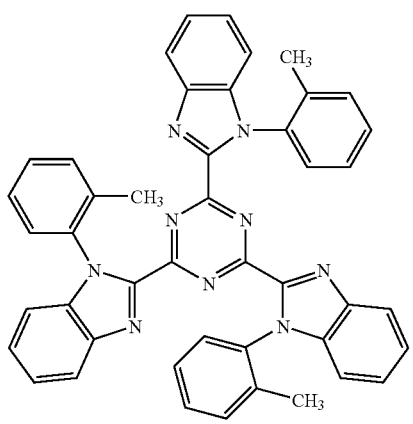
(B-15)

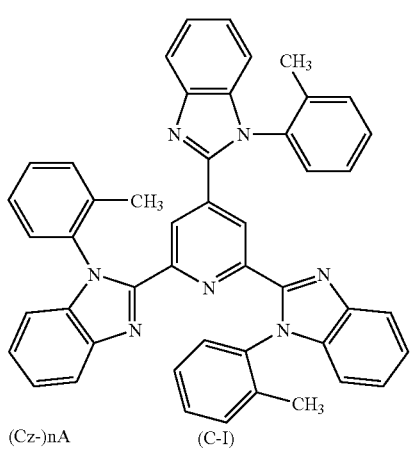
(B-16)

(Cz-)nA     (C-I)
Cz(-A)m     (C-II)

where Cz represents a substituted or unsubstituted carbazolyl group, an aryl carbazolyl group, or a carbazolylalkylene group, A represents a group formed of a site represented by the following general formula (A), and n and m each represent an integer of 1 to 3:

(M)p-(L)q-(M')r     (A)

where M and M' each independently represent a nitrogen-containing heteroaromatic ring which is formed of 2 to 40 carbon atoms and which may have, or may be free of, a substituent, and M and M' may be identical to or different from each other, L represents a single bond, an arylene group having 6 to 30 carbon atoms, a cycloalkylene group having 5 to 30 carbon atoms, or a heteroaromatic ring which has 2 to 30 carbon atoms and which may have, or may be free of, a substituent bonded to the ring, and p represents an integer of 0 to 2, q represents an integer of 1 or 2, and r represents an integer of 0 to 2 provided that p+r is equal to or larger than 1.

The bonding manner of each of the general formulae (C-I) and (C-II) is specifically represented as shown in the following table depending on a number represented by each of the parameters n and m.

| n = m = 1 | n = 2 | n = 3 | m = 2 | m = 3 |
|---|---|---|---|---|
| Cz-A | Cz-A-Cz | Cz-A-Cz<br>      |<br>      Cz | A-Cz-A | A-Cz-A<br>      |<br>      A |

In addition, the bonding manner of the group represented by the general formula (A) is specifically any one of the forms shown in the items (1) to (16) in the following table depending on a number represented by each of the parameters p, q, and r.

| No | p | q | r | Bonding manner |
|---|---|---|---|---|
| (1) | 0 | 1 | 1 | L—M' |
| (2) | 0 | 1 | 2 | L—M'—M', M'—L—M' |
| (3) | 0 | 2 | 1 | L—L—M', L—M'—L |
| (4) | 0 | 2 | 2 | L—L—M'—M', M'—L—L—M', 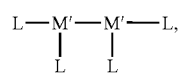 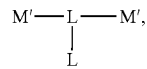 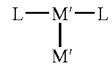 |
| (5) | 1 | 1 | 0 | Identical to (1) (M' is exchanged for M) |
| (6) | 1 | 1 | 1 | M—L—M' |
| (7) | 1 | 1 | 2 | M—L—M'—M', 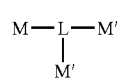 |
| (8) | 1 | 2 | 0 | Identical to (3) (M' is exchanged for M) |
| (9) | 1 | 2 | 1 | M—L—L—M', L—M—L—M', M—L—M'—L |
| (10) | 1 | 2 | 2 | M—L—L—M'—M', M'—L—M—L—M', M'—M'—L—M—L, 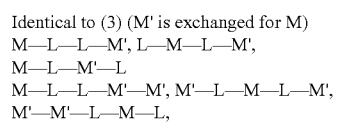 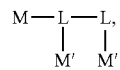 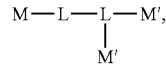 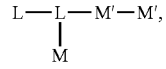 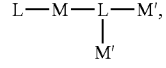 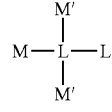 |
| (11) | 2 | 1 | 0 | Identical to (2) (M' is exchanged for M) |
| (12) | 2 | 1 | 1 | Identical to (7) (M' is exchanged for M) |

-continued

| No | p | q | r | Bonding manner |
|---|---|---|---|---|
| (13) | 2 | 1 | 2 | M—M—L—M'—M', |
| | | | | M—L(—M')(—M')—M, |
| | | | | M—L(—M)—M'—M' |
| (14) | 2 | 2 | 0 | Identical to (4) (M' is exchanged for M) |
| (15) | 2 | 2 | 1 | Identical to (10) (M' is exchanged for M) |
| (16) | 2 | 2 | 2 | M—M—L—L—M'—M', |
| | | | | M—M—L(—L)—M'—M', |
| | | | | M—L—L(—M)—M'—M', |
| | | | | M—L(—M)(—M')(—M')—L, |
| | | | | M—M—L—L(—M')—M', |
| | | | | L—L(—M)(—M)—M'—M', |
| | | | | M—L(—M')—L(—M')—M |

When Cz is bonded to A in each of the general formulae (C-I) and (C-II), Cz may be bonded to any one of M, L, and M' representing A. For example, in Cz-A for m=n=1, in the case of p=q=r=1 (the item (6) in the table), A represents M-L-M', so three bonding manners are available: Cz-M-L-M', M-L(-Cz)-M', and M-L-M'-Cz. In addition, similarly, for example, in Cz-A-Cz for n=2 in the general formula (C-1), in the case of p=q=1 and r=2 (the item (7) in the table), A represents M-L-M'-M' or M-L(-M')-M', so the following bonding manners are available.

Cz—M(—Cz)—L—M'—M', Cz—M—L(—Cz)—M'—M',

Cz—M—L—M'(—Cz)—M', Cz—M—L—M'—M'—Cz,

M—L(—Cz)(—Cz)—M'—M', M—L(—Cz)—M'(—Cz)—M',

M—L—M'—M'—Cz (with Cz branches), M—L—M'—M' (with Cz branches),

Cz—M—L—M', Cz—M—L—M',
(with Cz, M' branches) (with M' branch)

Cz—M—L—M' (with M', Cz branches), M—L—M' (with Cz, Cz, M' branches), M—L—M'—Cz (with Cz, M' branches), M—L—M' (with Cz—M'—Cz below), M—L—M'—Cz (with M'—Cz below).

Specific examples of the structure represented by each of the general formulae (C-I) and (C-II) include the following structures. However, the structure is not limited to the examples.

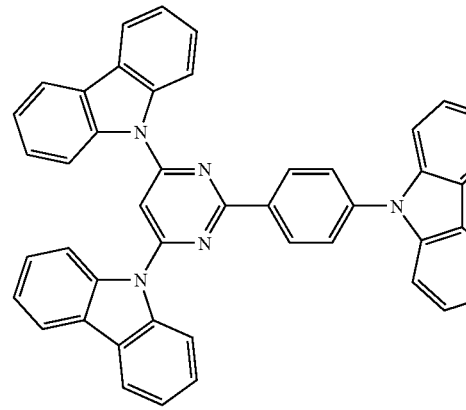

(C-1)

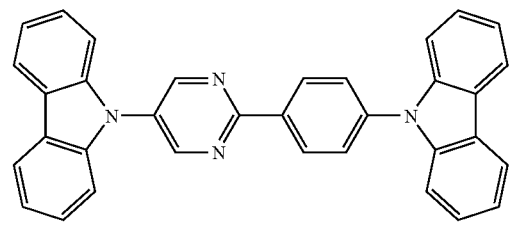

(C-2)

(C-3)
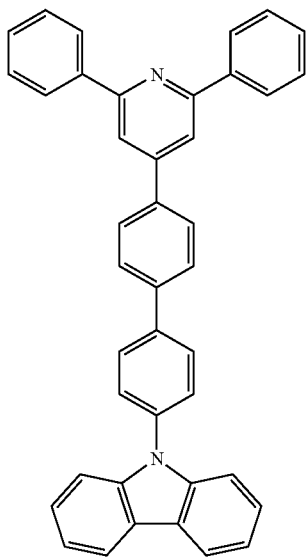
(C-4)
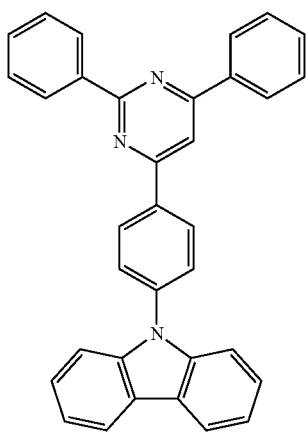
(C-5)
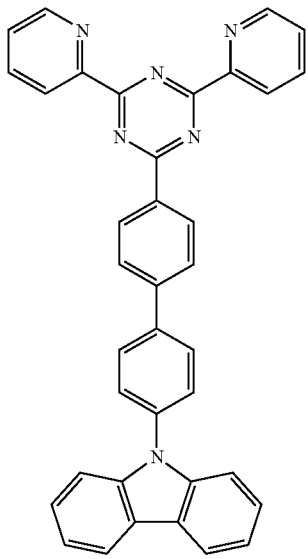
(C-6)
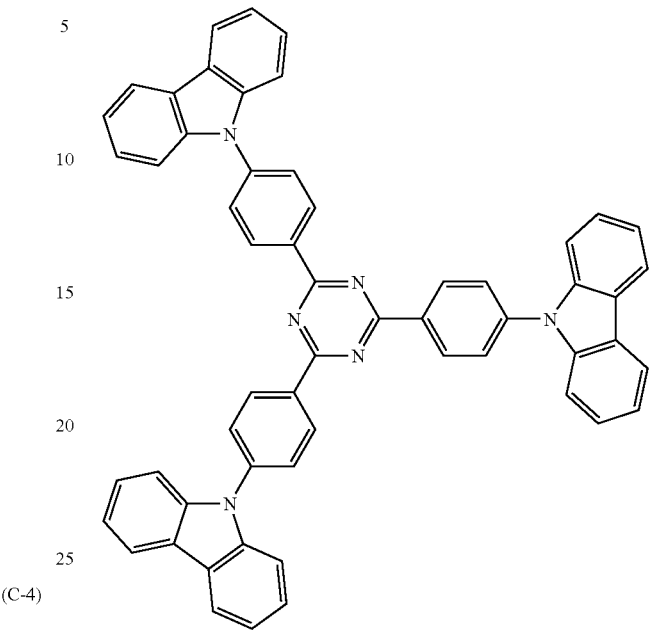
(C-7)
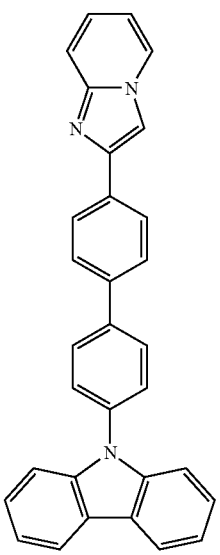

-continued
(C-8)
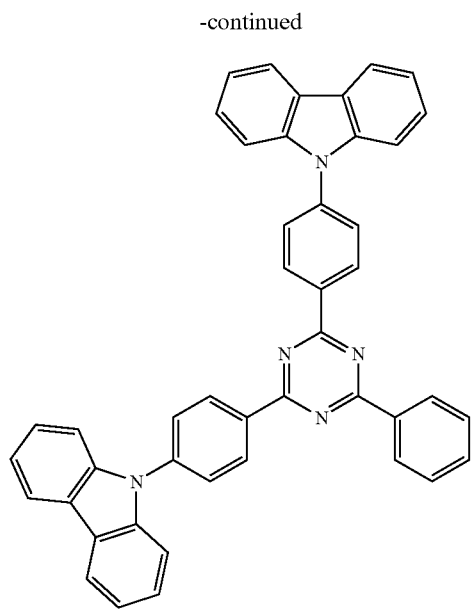
(C-9)
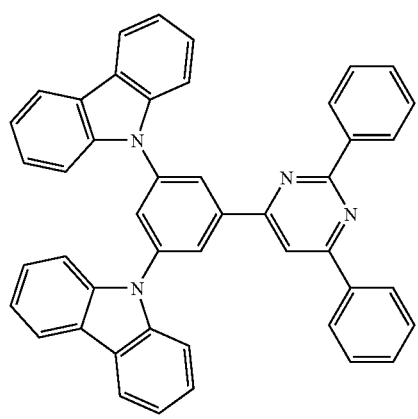
(C-10)
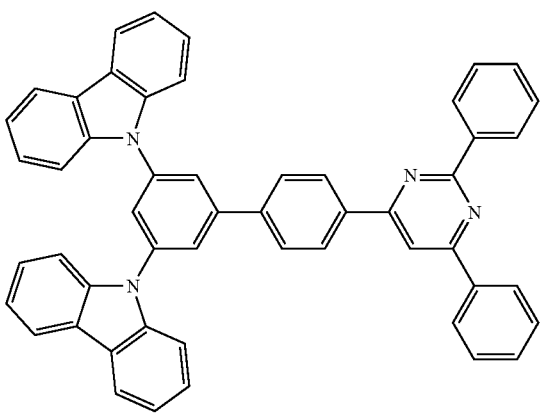
-continued
(C-11)
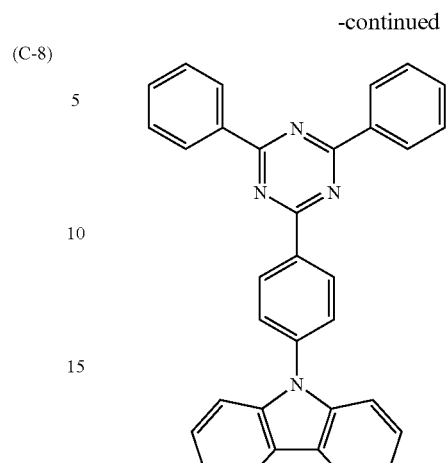
(C-12)
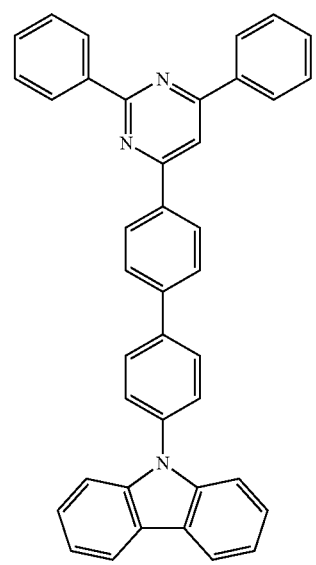
(C-13)
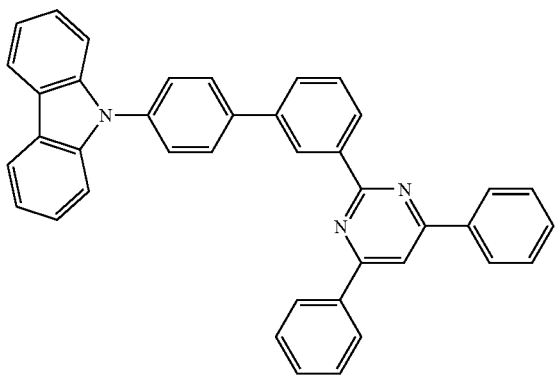

-continued (C-14)

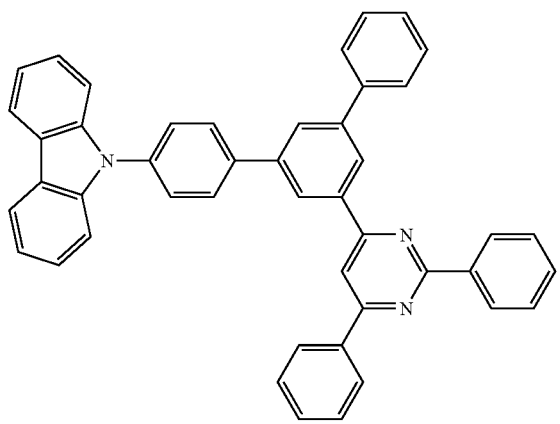

(C-15)

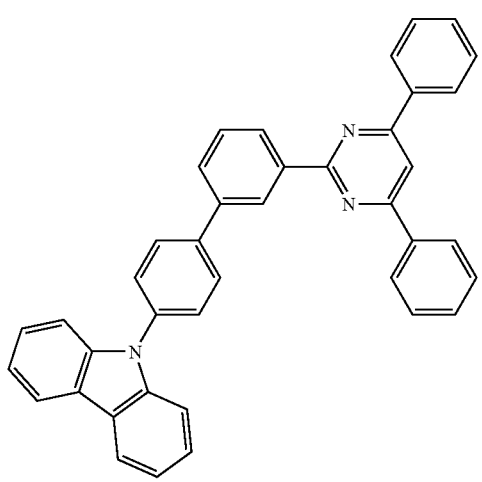

(C-III)

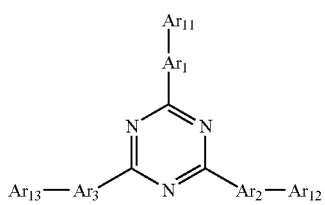

where $Ar_{11}$ to $Ar_{13}$ each represent a group similar to $R^{B2}$ of the general formula (B-I), and specific examples of $Ar_{11}$, to $Ar_{13}$ include examples similar to those of $R^{B2}$, and $Ar_1$ to $Ar_3$ each represent a group obtained by making a group similar to $R^{B2}$ of the general formula (B-I) divalent, and specific examples of $Ar_1$ to $Ar_3$ include examples obtained by making examples of $R^{B2}$ divalent.

A specific example of the general formula (C-III) is shown below. However, the formula is not limited to the example.

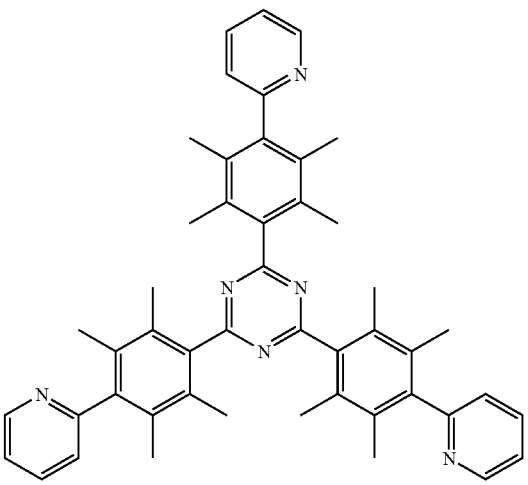

(C-IV)

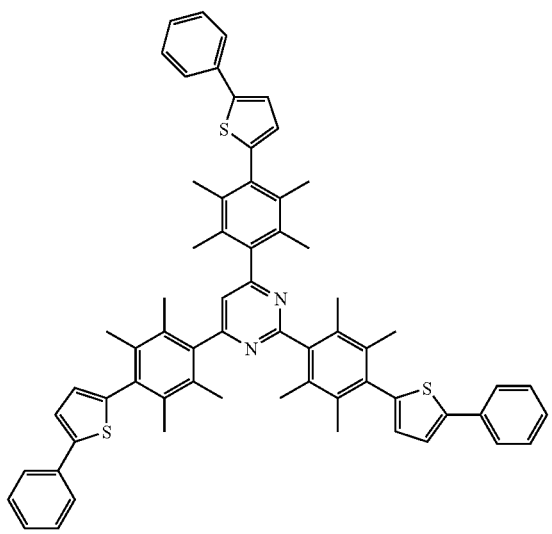

where $R^{11}$ to $R_{14}$ each represent a group similar to $R^{B2}$ of the general formula (B-I), and specific examples of $R^{11}$ to $R_{14}$ include examples similar to those of $R^{B2}$.

Specific examples of the general formula (C-IV) are shown below. However, the formula is not limited to the examples.

-continued

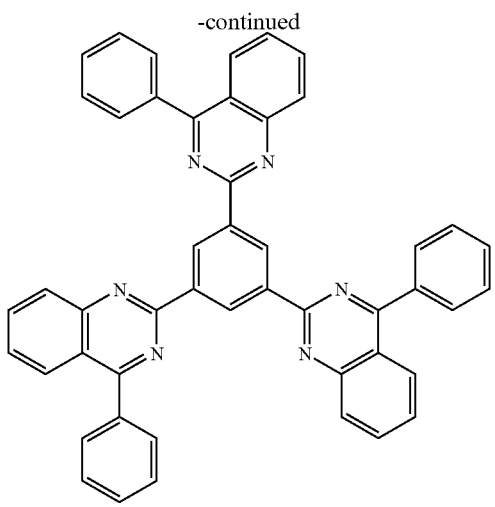

(C-V)

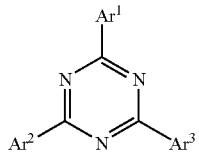

where $Ar^1$ to $Ar^3$ each represent a group similar to $R^{B2}$ of the general formula (B-I), and specific examples of $Ar^1$ to $Ar^3$ include examples similar to those of $R^{B2}$.

A specific example of the general formula (C-V) is shown below. However, the formula is not limited to the example.

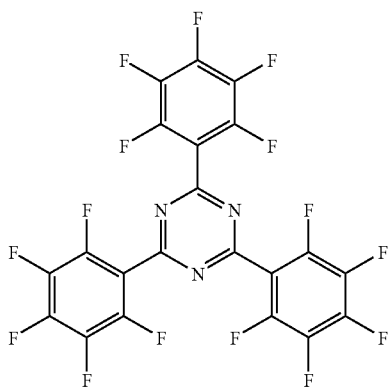

(C-VI)

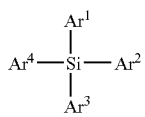

where $Ar^1$ to $Ar^4$ each represent a group similar to $R^{B2}$ of the general formula (B-I), and specific examples of $Ar^1$ to $Ar^4$ include examples similar to those of $R^{B2}$.

A specific example of the general formula (C-VI) is shown below. However, the formula is not limited to the example.

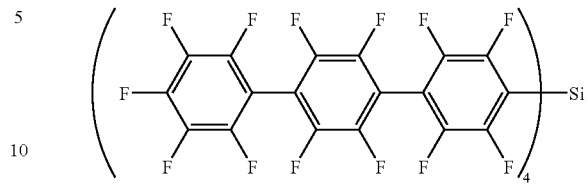

In addition, in the organic EL device of the present invention, an insulating or semi-conducting, inorganic compound is preferably used as a substance constituting the electron injecting or transporting layer. When the electron injecting or transporting layer is constituted by an insulator or a semiconductor, a current leak can be effectively prevented, and electron injecting property can be improved. It is preferable that at least one metal compound selected from the group consisting of alkali metal chalcogenides, alkaline earth metal chalcogenides, alkali metal halides, and alkaline earth metal halides be used as such the insulator. It is preferable that the electron injecting or transporting layer be constituted with the above-mentioned alkali metal chalcogenide since the electron injecting property can be improved.

To be specific, preferable examples of the alkali metal chalcogenide include $Li_2O$, $LiO$, $Na_2S$, $Na_2Se$, and $NaO$. Preferable examples of the alkaline earth metal chalcogenide include $CaO$, $BaO$, $SrO$, $BeO$, $BaS$, and $CaSe$. Preferable examples of the alkali metal halide include $LiF$, $NaF$, $KF$, $LiCl$, $KCl$, and $NaCl$. Preferable examples of the alkaline earth metal halide include fluorides such as $CaF_2$, $BaF_2$, $SrF_2$, $MgF_2$, and $BeF_2$, and halides other than the fluorides.

Further, examples of the semiconductor for constituting the electron injecting or transporting layer include oxides, nitrides, and oxide nitrides containing at least one element selected from the group consisting of Ba, Ca, Sr, Yb, Al, Ga, In, Li, Na, Cd, Mg, Si, Ta, Sb, and Zn, which are used alone or in combination of two or more. It is preferable that the inorganic compound constituting the electron transporting layer be in the form of a fine crystalline or amorphous insulating thin film. When the electron transporting layer is constituted of the above-mentioned insulating thin film, a more uniform thin film can be formed, and defective pixels such as dark spots can be decreased. Examples of the inorganic compound include the alkali metal chalcogenides, the alkaline earth metal chalcogenides, the alkali metal halides, and the alkaline earth metal halides which are described above.

Further, in the organic EL device of the present invention, at least one of the electron injecting layer and the electron transporting layer may contain a reducing dopant having a work function of 2.9 eV or less. The term "reducing dopant" as used herein refers to a compound that increases the efficiency with which an electron is injected.

In addition, in the present invention, a reducing dopant is preferably added to an interfacial region between the cathode and the organic thin film layer so that at least part of an organic layer in the interfacial region is reduced and turned into an anion. A preferable reducing dopant is at least one compound selected from the group consisting of an alkali metal, an oxide of an alkali earth metal, an alkali earth metal, a rare earth metal, an oxide of an alkali metal, a halide of an alkali metal, a halide of an alkali earth metal, an oxide or halide of a rare earth metal, an alkali metal complex, an alkali earth metal complex, and a rare earth metal complex. To be specific, a preferable reducing dopant is at least one alkali metal selected from the group consisting of Na (work function: 2.36 eV), K (work function: 2.28 eV), Rb (work function: 2.16 eV), and Cs (work function: 1.95 eV) or at least one alkali earth metal selected from the group consisting of Ca (work function: 2.9 eV), Sr (work function: 2.0 to 2.5 eV), and Ba (work function: 2.52 eV); a reducing dopant having a work function of 2.9 eV is particularly preferable. Of those, a more preferable reducing dopant is at least one alkali metal selected from the group consisting of K, Rb, and Cs, a still more preferable reducing dopant is Rb or Cs, and the most preferable reducing dopant is Cs. Those alkali metals each have a particularly high reducing ability. The addition of a relatively small amount of each of those alkali metals to a region into which an electron is injected can improve the emission luminance and lifetime of the organic EL device.

Preferable examples of the alkali earth metal oxide include BaO, SrO, CaO, $Ba_xSr_{1-x}O$ ($0<x<1$) obtained by mixing BaO and SrO, and $Ba_xCa_{1-x}O$ ($0<x<1$) obtained by mixing BaO and CaO. Examples of an alkali oxide or an alkali fluoride include LiF, $Li_2O$, and NaF. The alkali metal complex is not particularly limited as long as it contains at least an alkali metal ion as a metal ion. The alkali earth metal complex is not particularly limited as long as it contains at least an alkali earth metal ion as a metal ion. The rare earth metal complex is not particularly limited as long as it contains at least a rare earth metal ion as a metal ion. In addition, examples of a ligand include, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxy fluborane, bipyridyl, phenanthroline, phthalocyanine, porphyrin, cyclopentadiene, β-diketones, azomethines, and derivatives of them.

In addition, the reducing dopant is preferably formed into a layer shape or an island shape. The thickness of the reducing dopant to be used in a layer shape is preferably 0.05 to 8 nm.

A preferable approach to forming an electron injecting or transporting layer containing the reducing dopant is a method involving: depositing organic matter as a light emitting material or electron injecting material for forming the interfacial region simultaneously with the deposition of the reducing dopant by a resistance heating deposition method; and dispersing the reducing dopant in the organic matter. A molar concentration ratio between the reducing dopant to be dispersed and the organic matter is 100:1 to 1:100, or preferably 5:1 to 1:5. Upon formation of the reducing dopant into a layer shape, the light emitting material or the electron injecting material is formed into a layer shape to serve as an interfacial organic layer, and then the reducing dopant is deposited alone by the resistance heating deposition method to be formed into a layer shape having a thickness of preferably 0.5 nm to 15 nm. Upon formation of the reducing dopant into an island shape, the light emitting material or the electron injecting material is formed to serve as an interfacial organic layer, and then the reducing dopant is deposited alone by the resistance heating deposition method to be formed into an island shape having a thickness of preferably 0.05 to 1 nm.

The light emitting layer of the organic EL device of the present invention has: a function with which a hole can be injected from the anode or the hole injecting layer and an electron can be injected from the cathode or the electron injecting layer upon application of an electric field; a function of moving injected charge (the electron and the hole) with the force of the electric field; and a function with which a field for recombination between the electron and the hole is provided so that the recombination can lead to light emission. The light emitting layer of the organic EL device of the present invention preferably contains at least the transition metal complex compound of the present invention, and may contain a host material using the transition metal complex compound as a guest material. Examples of the host material include a host material having a carbazole skeleton, a host material having a diarylamine skeleton, a host material having a pyridine skeleton, a host material having a pyrazine skeleton, a host material having a triazine skeleton, and a host material having an arylsilane skeleton. The energy level of the lowest triplet excited state (Tl) of the host material is preferably larger than the Tl level of the guest material. The host material may be a low-molecular-weight compound, or may be a high-molecular-weight compound. In addition, a light emitting layer in which the host material is doped with a light emitting material such as the transition metal complex compound can be formed by, for example, the co-deposition of the host material and the light emitting material.

A method of forming each of the layers in the organic EL device of the present invention is not particularly limited. Various methods such as a vacuum deposition method, an LB method, a resistance heating deposition method, an electron beam method, a sputtering method, a molecular lamination method, a coating method (such as a spin coating method, a cast method, or a dip coating method), an ink-jet method, and a printing method can be employed. In the present invention, a coating method as an application method is preferable.

Further, the organic thin film layer containing the transition metal complex compound of the present invention can be formed in accordance with a conventionally known method such as the vacuum deposition method, the molecular beam epitaxy method (i.e., MBE method), or the coating method such as the dipping method, the spin coating method, the casting method, a bar coat method, and a roll coat method, each of which uses a solution with a substance dissolved in a solvent.

Each layer can be formed by the coating method, which involves: dissolving the transition metal complex compound of the present invention in a solvent to prepare an application liquid; applying the application liquid onto a desired layer (or electrode); and drying the liquid. The application liquid may contain a resin, and the resin may be in a dissolved state or in a dispersed state in the solvent. A disconjugate polymer (such as polyvinyl carbazole) or a conjugate polymer (such as a polyolefin-based polymer) can be used as the resin. To be specific, examples of the resin include polyvinyl chloride, polycarbonate, polystyrene, polymethyl methacrylate, polybutyl methacrylate, polyester, polysulfone, polyphenylene oxide, polybutadiene, poly(N-vinylcarbazole), a hydrocarbon resin, a ketone resin, a phenoxy resin, polyamide, ethyl cellulose, vinyl acetate, an ABS resin, polyurethane, a melamine resin, an unsaturated polyester resin, an alkyd resin, an epoxy resin, and a silicone resin.

In addition, the thickness of each organic layer of the organic EL device of the present invention is not particularly limited. In general, however, an excessively small thickness is apt to generate defects such as a pinhole, and an excessively large thickness requires a high applied voltage, thereby resulting in poor efficiency. Accordingly, the thickness is preferably in the range of several nanometers to 1 μm in ordinary cases.

EXAMPLES

Next, the present invention will be described in more detail by way of examples.

Example 1

Synthesis of Transition Metal Complex Compound 8

(1) Synthesis of Compound 3

Compound 3 was synthesized in accordance with the following process.

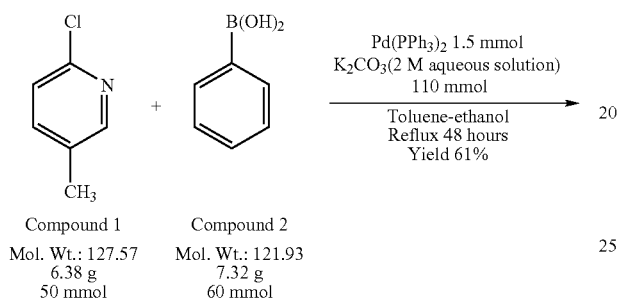

Compound 1
Mol. Wt.: 127.57
6.38 g
50 mmol

Compound 2
Mol. Wt.: 121.93
7.32 g
60 mmol

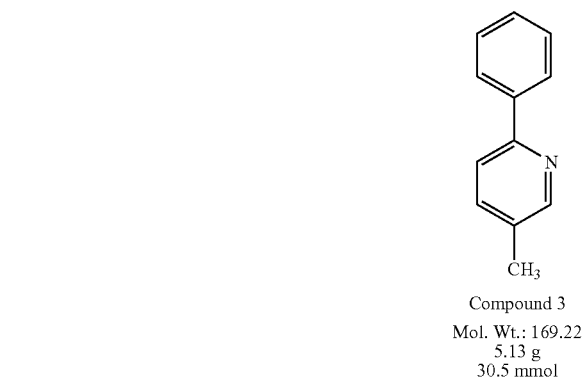

Compound 3
Mol. Wt.: 169.22
5.13 g
30.5 mmol

In a stream of argon, 6.38 g (molecular weight 127.57, 50 mmol) of Compound 1, 7.32 g (molecular weight 121.93, 60 mmol) of Compound 2, and 1.73 g (molecular weight 1,155.56, 1.5 mmol) of tetrakis(triphenylphosphine)palladium(0) were sequentially added with 130 ml of toluene and 20 ml of ethanol in the stated order. Further, 55 ml of a 2-mol/l aqueous solution of potassium carbonate (molecular weight 99.11, 10.9 g, 110 mmol) were added to the mixture, and the whole was refluxed for 48 hours. After the reaction liquid had been cooled, an aqueous layer was separated from the reaction liquid by using a separating funnel, and was then subjected to an extraction operation with methylene chloride twice. An oil layer was dried with anhydrous magnesium sulfate, and a volatile component was removed by distillation under reduced pressure, whereby a coarse product was obtained. Further, the coarse product was purified by means of silica gel column chromatography (using a mixed solvent of hexane and ethyl acetate at a ratio of 10:1 as a developing solvent), whereby 5.13 g (molecular weight 169.22, 30.5 mmol, 61% yield) of Compound 3 as a target were obtained.

(2) Synthesis of Compound 5

Compound 5 was synthesized in accordance with the following process.

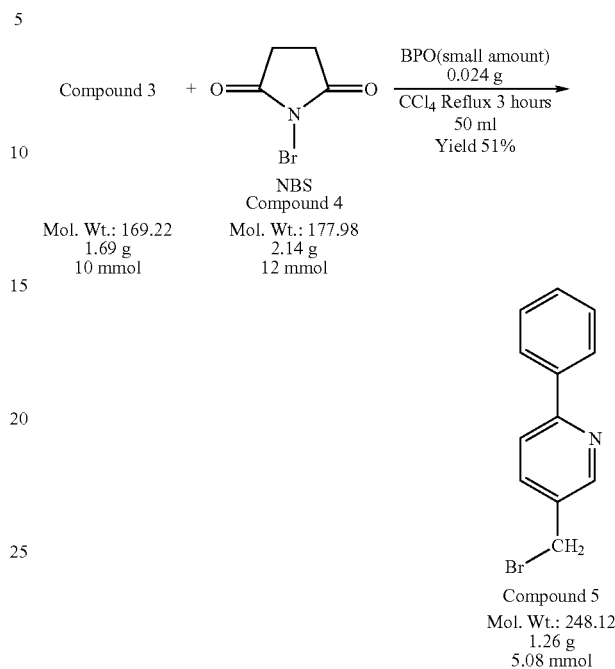

NBS: N-bromosuccinimide
BPO: Benzoyl peroxide

In a stream of argon, 1.69 g (molecular weight 169.22, 10 mmol) of Compound 3 obtained in the above item (1) and 2.14 g (molecular weight 177.98, 12 mmol) of Compound 4 were loaded into 50 ml of carbon tetrachloride. Further, a small amount (0.024 g) of benzoyl peroxide was added to the mixture, and the whole was refluxed for 3 hours. The temperature of the reaction liquid was returned to room temperature, the resultant solid component (succinimide) was separated by filtration, and the solvent (carbon tetrachloride) was removed by distillation under reduced pressure, whereby a coarse product was obtained. Further, the coarse product was purified by means of silica gel chromatography (using a mixed solvent of hexane and ethyl acetate at a ratio of 10:1 as a developing solvent), whereby 1.26 g (molecular weight 248.12, 5.08 mmol, 51% yield) of Compound 5 were obtained.

(3) Synthesis of Compound 7

Compound 7 was synthesized in accordance with the following process.

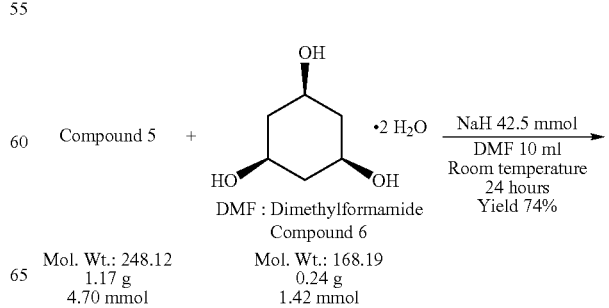

DMF: Dimethylformamide

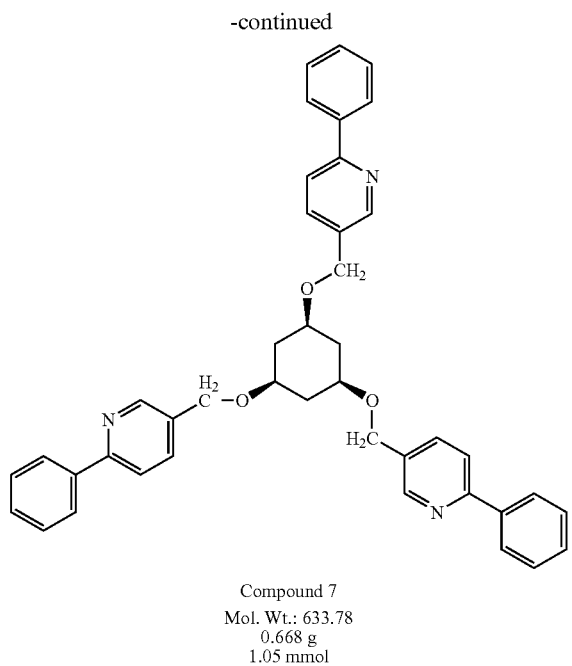

Compound 7
Mol. Wt.: 633.78
0.668 g
1.05 mmol

In a stream of argon, 1.17 g (molecular weight 248.12, 4.70 mmol) of Compound 5, 0.24 g (molecular weight 168.19, 1.42 mmol) of Compound 6, and 1.7 g (1.02 g in terms of sodium hydride, 42.5 mmol) of 60% sodium hydride (mineral oil dispersion) were added with 10 ml of dimethylformamide (DMF), and the whole was stirred at room temperature for 24 hours. After the completion of the reaction, the reaction liquid was poured into ice water, and the whole was subjected to an extraction operation with methylene chloride 3 times. Next, methylene chloride was removed by distillation under reduced pressure, whereby a coarse product was obtained. Further, the coarse product was purified by means of silica gel chromatography (using a mixed solvent of hexane and ethyl acetate at a ratio of 1:1 as a developing solvent), whereby 0.668 g (molecular weight 633.78, 1.05 mmol, 74% yield) of Compound 7 was obtained.

(4) Synthesis of Compound 8

Compound 8 was synthesized in accordance with the following process.

Compound 7
Mol. Wt.: 633.78
0.12 g
0.190 mmol

IrCl·nH$_2$O 0.068 g
(about 1.2 equivalents)
CF$_3$COOAg 0.17 g
(4.0 equivalents)
────────────────→
o•Dichlorebenzene 30 ml
H$_2$O 2 ml
Reflux 4 hours
Yield 3.1%

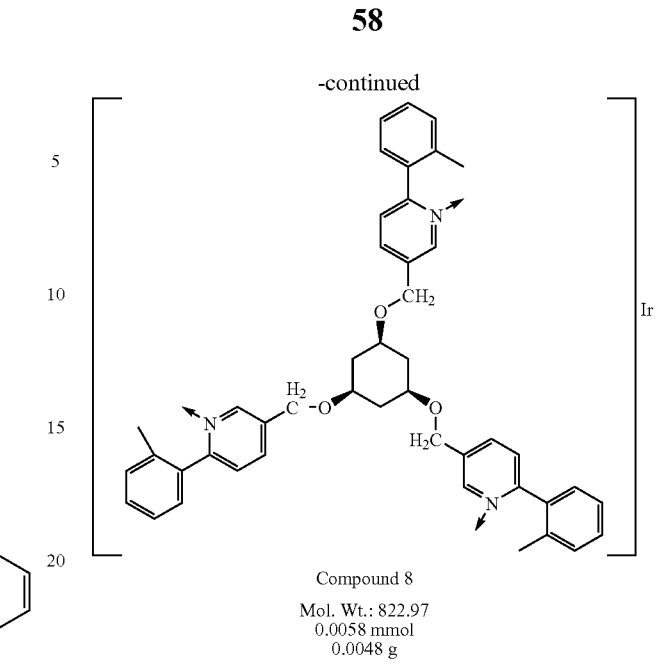

Compound 8
Mol. Wt.: 822.97
0.0058 mmol
0.0048 g

In a stream of argon, 0.12 g (molecular weight 633.78, 0.19 mmol) of Compound 7, 0.068 g of iridium trichloride hydrate, and 0.17 g (molecular weight 220.88, 0.77 mmol) of silver trifluoroacetate were added to a mixed solvent of 30 ml of 1,2-dichlorobenzene and 2 ml of water, and the whole was refluxed under heat for 4 hours. After the temperature of the reaction liquid had been cooled to room temperature, the reaction liquid was passed through a silica gel by using a mixed liquid of methylene chloride and hexane (at a ratio of 50:50), whereby Compound 8 as a target was obtained (yellow solid, molecular weight 822.97, 4.8 mg, 3.1% yield).

The following items (1) to (4) of the resultant compound (Compound 8) were measured.

<Various Results of Measurement>

(1) FD-MS measurement: the maximum peak value was 823, and coincided with a calculated value (calculated value M$^+$ (molecular ion peak)=823).

The FD-MS measurement (field desorption ionization mass spectrometry) was performed under the following conditions.

Device: HX 110 (manufactured by JEOL Ltd.)

Conditions: acceleration voltage 8 kV scan range m/z=50 to 1,500 emitter kind carbon emitter current 0 mA→2 mA/min→40 mA (held for 10 minutes)

Figure 2:
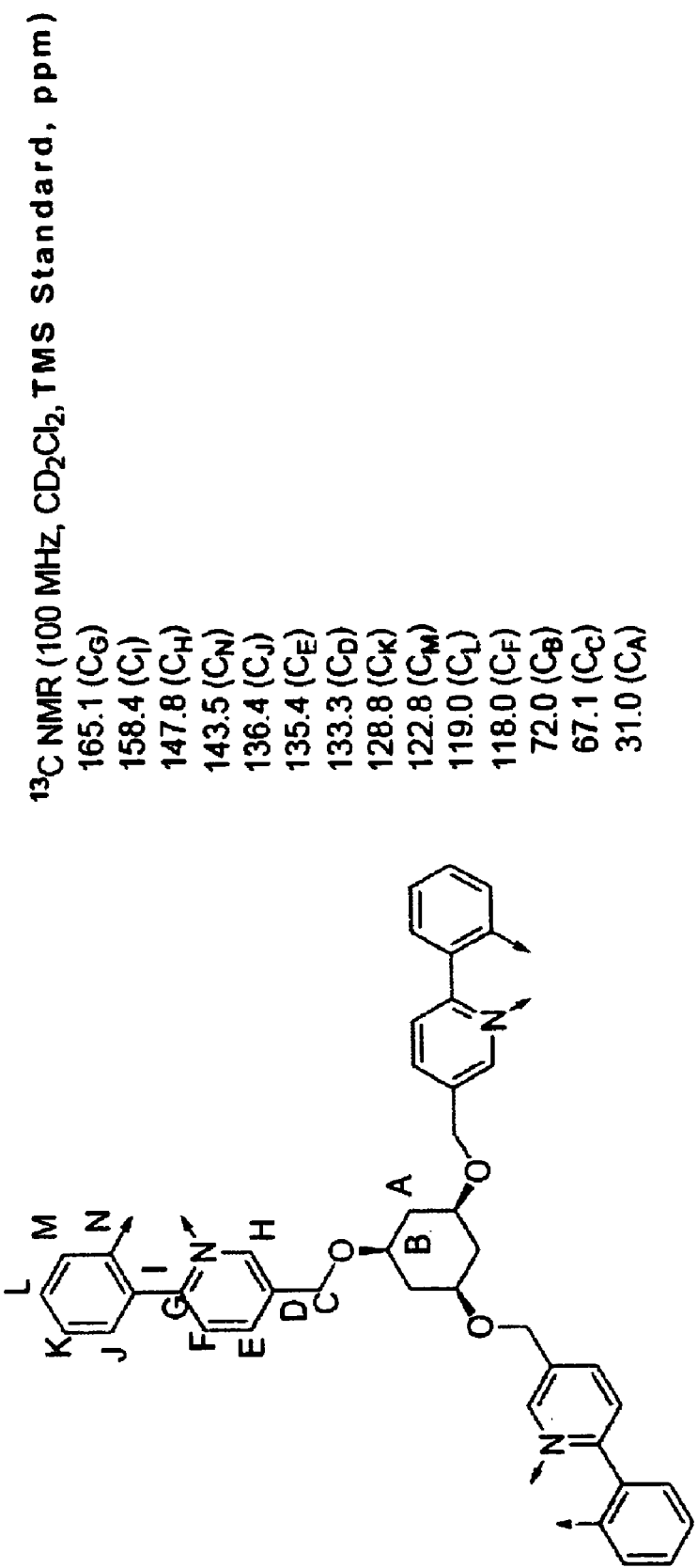
[FIG. 2] A view showing $^{13}$C-NMR spectrum data on Metal Complex Compound 8 obtained in Example 1.

(2) NMR measurement: attribution was performed as described below by $^1$H-NMR, $^{13}$C-NMR, H—H COSY (homogeneous nuclear correlation two-dimensional NMR spectrum), HMQC (heterogeneous nuclear multi-quantum correlation two-dimensional NMR spectrum), HMBC (heterogeneous nuclear remote multi-quantum correlation two-dimensional NMR spectrum), and NOESY (nuclear Overhauser effect correlation two-dimensional NMR spectrum) (FIG. 1: $^1$H-NMR, FIG. 2: $^{13}$C-NMR).

NMR device name: JEOL JNM-ECP 400 ($^1$H-NMR: 400 MHz, $^{13}$C-NMR: 100 MHz)

Measurement solvent: solvent CD$_2$Cl$_2$ (deuterated methylene chloride), standard 0.00 ppm (tetramethylsilane)

Figure 3:
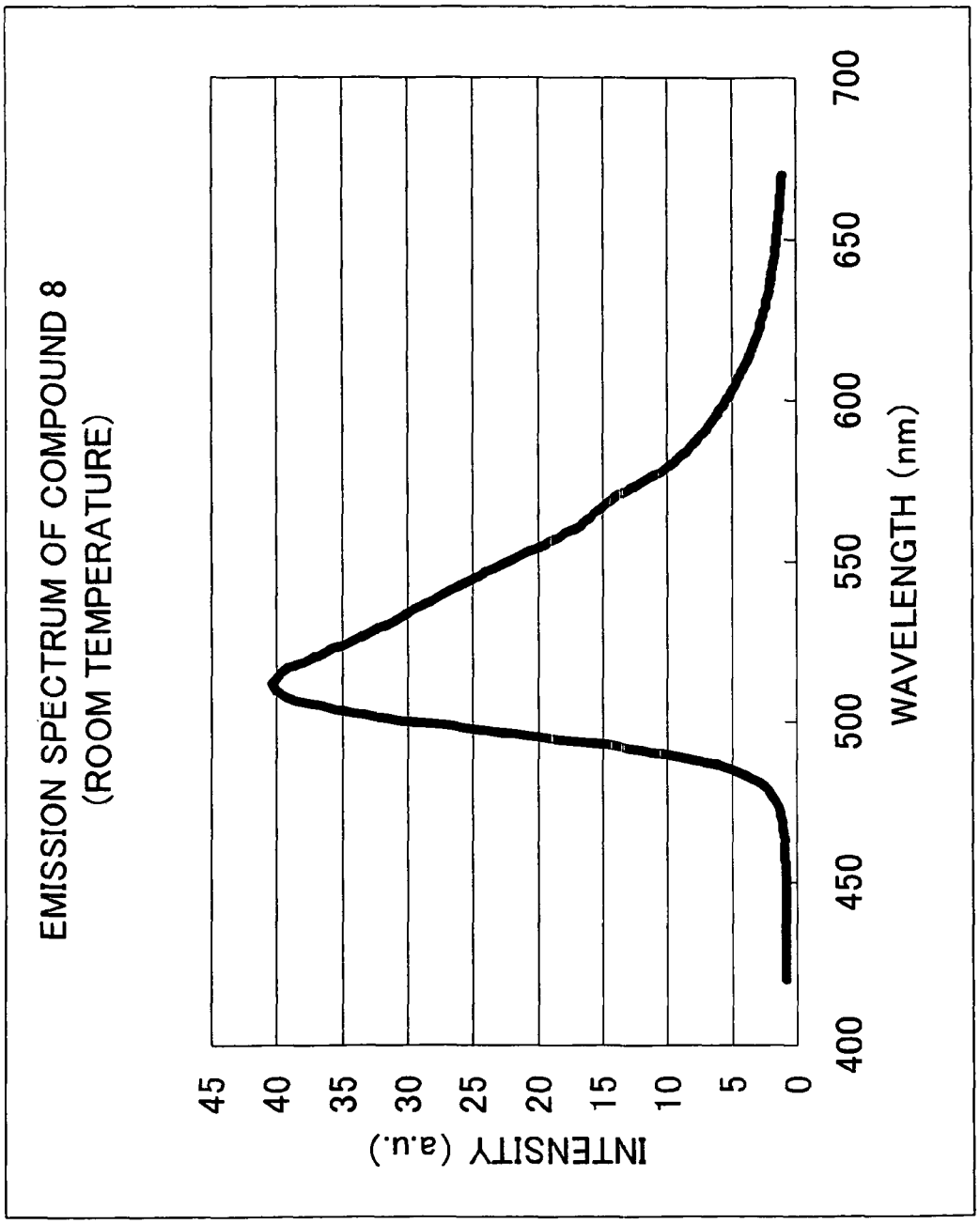
[FIG. 3] A view showing the emission spectrum of Metal Complex Compound 8.

(3) Measurement of emission spectrum (room temperature): see FIG. 3

Device: F-4500 spectrofluorometer

Measurement solvent: methylene chloride

FIG. 3 shows that light was emitted in a solution state (maximum luminous wavelength $\lambda_{max}$=512 nm).

Figure 4:
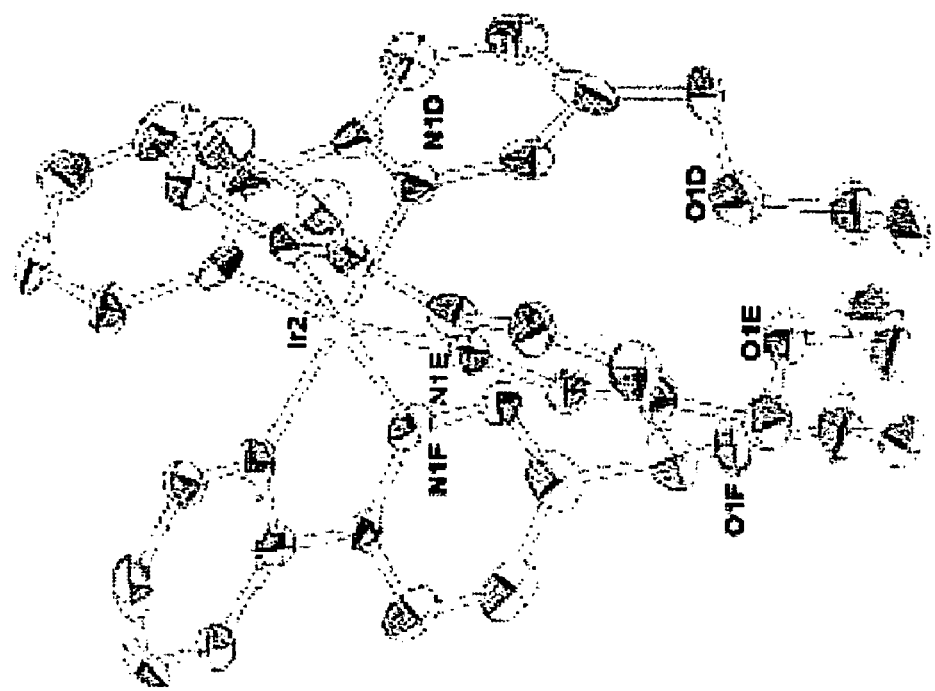
[FIG. 4] A view showing the X-ray crystallography of Metal Complex Compound 8.
Figure 4:
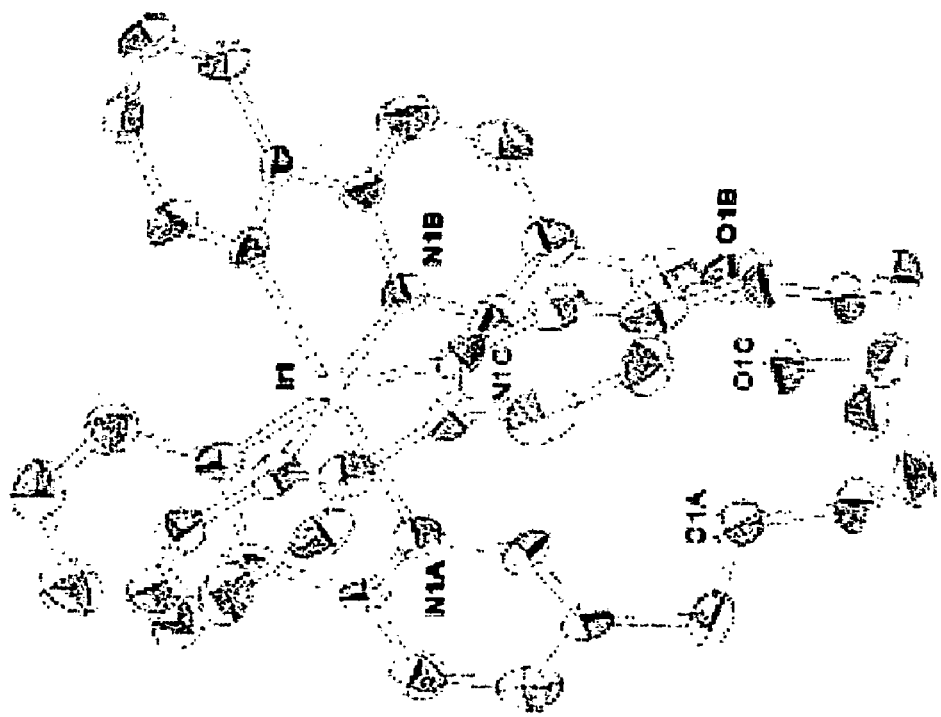

(4) X-ray crystallography: see FIG. 4

Device: Rigaku PAXIS-RAPID Imaging Plate Diffractometer

Example 2

Synthesis of Transition Metal Complex Compound 15

(1) Synthesis of Compound 10

Compound 10 was synthesized in accordance with the following process.

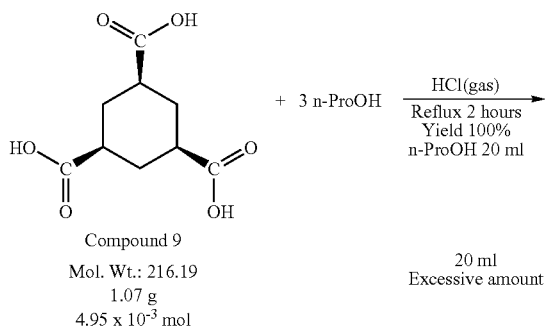

n-Pro = n-propyl group 1.07 g of Compound 9 were added to and suspended into 20 ml of dry 1-propanol. A hydrogen chloride gas was bubbled in the suspension for 2 hours. While the bubbling was continued, the temperature of the reaction solution was increased, and the reaction solution was refluxed for 1 hour, and was then subjected to a reaction. After the completion of the reaction, the temperature of the resultant was returned to room temperature, and a volatile component was removed by distillation under reduced pressure. Cold water was added to the oily residue, and the whole was extracted with diethyl ether. Next, the diethyl ether solution was dried (dehydrated) with anhydrous magnesium sulfate and filtered, and a volatile component was removed by distillation under reduced pressure, whereby 1.69 g of Compound 10 as a target in the form of colorless oily matter were obtained (100% yield).

(2) Synthesis of Compound 11

Compound 11 was synthesized in accordance with the following process.

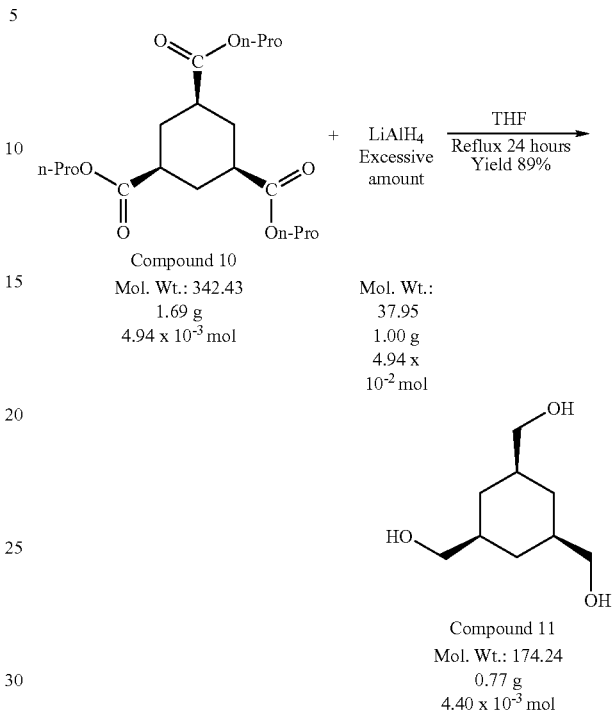

A reaction was performed in a stream of an inert gas.

1.0 g of lithium aluminum hydride (LiAlH$_4$) was added to 10 ml of dry tetrahydrofuran (THF). A solution of Compound 10 obtained in the above item (1) in THF (20 ml) was slowly dropped to the resultant under ice cooling. The temperature of the reaction solution was increased, and the reaction solution was refluxed for 24 hours. After the completion of the reaction, the temperature of the reaction solution was cooled to 0° C., and then ethanol and water were added in the stated order to the reaction solution to decompose an excessive hydride. The solid matter was filtered, and a volatile component was removed by distillation under reduced pressure, whereby 0.77 g of Compound 11 as a target in the form of a white solid was obtained (89% yield).

(3) Synthesis of Compound 11

Compound 11 was synthesized in accordance with the following process.

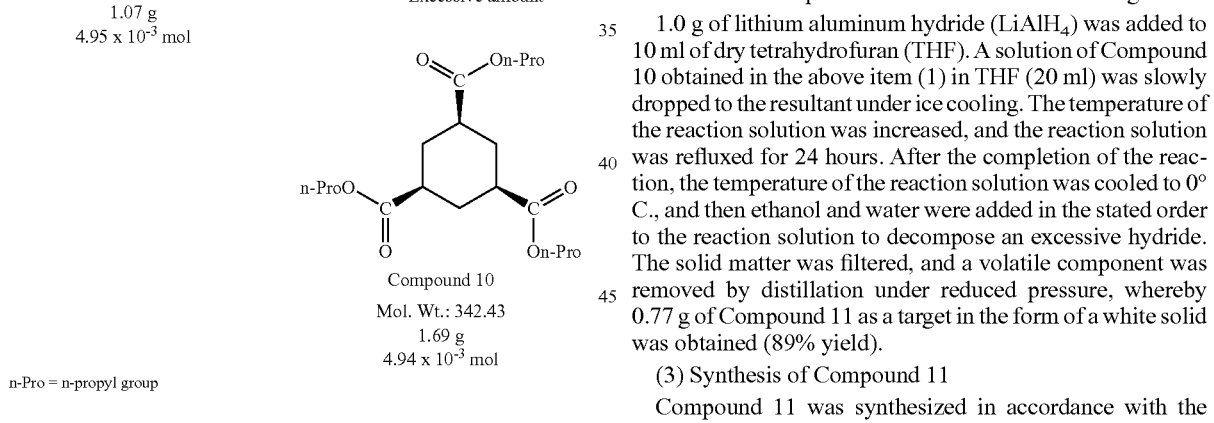

-continued

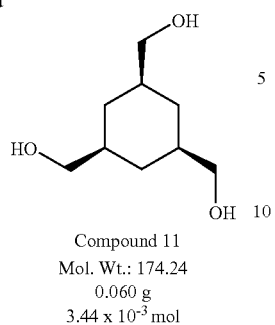

Compound 11
Mol. Wt.: 174.24
0.060 g
3.44 x 10⁻³ mol

A reaction was performed in a stream of an inert gas.

0.54 g of lithium aluminum hydride (LiAlH$_4$) was added with 2 ml of dry THF. Subsequently, a solution of Compound 9 (0.10 g) in THF (3 ml) was slowly dropped to the resultant at 0° C. After that, the temperature of the resultant was increased to room temperature, and, furthermore, the resultant was refluxed for 14 hours. After the completion of the reaction, a 3N aqueous solution of NaOH was added to the resultant at 0° C. until the generation of hydrogen stopped. The reaction liquid was filtered while being passed through Celite, and the solvent was removed by distillation, whereby 0.060 g of Compound 11 as a target in the form of a white solid was obtained (74% yield).

(4) Synthesis of Compound 12

Compound 12 was synthesized in accordance with the following process.

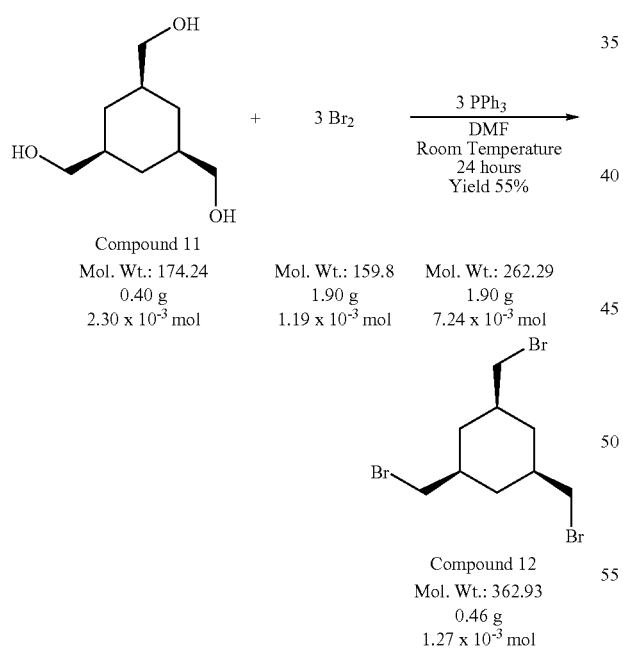

A reaction was performed in a stream of an inert gas.

Compound 11 (0.40 g) obtained in the above item (2) and triphenylphosphine (1.90 g) were dissolved in 10 ml of dry DMF. While the mixture was sufficiently stirred at room temperature, bromine (1.90 g) was slowly dropped to the mixture, and the whole was stirred for 24 hours. DMF was removed by distillation under reduced pressure, whereby a reddish orange viscous liquid was obtained. Further, the liquid was purified by means of silica gel column chromatography, whereby 0.46 g of Compound 12 as a target in the form of a white solid was obtained (55% yield).

(5) Synthesis of Compound 14

Compound 14 was synthesized in accordance with the following process.

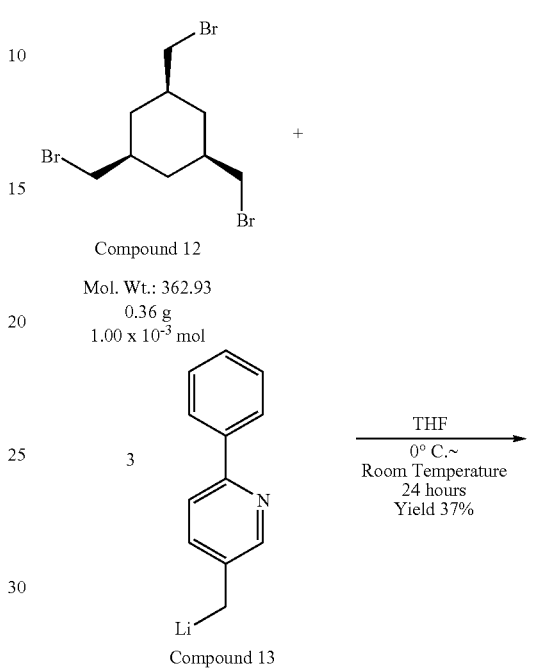

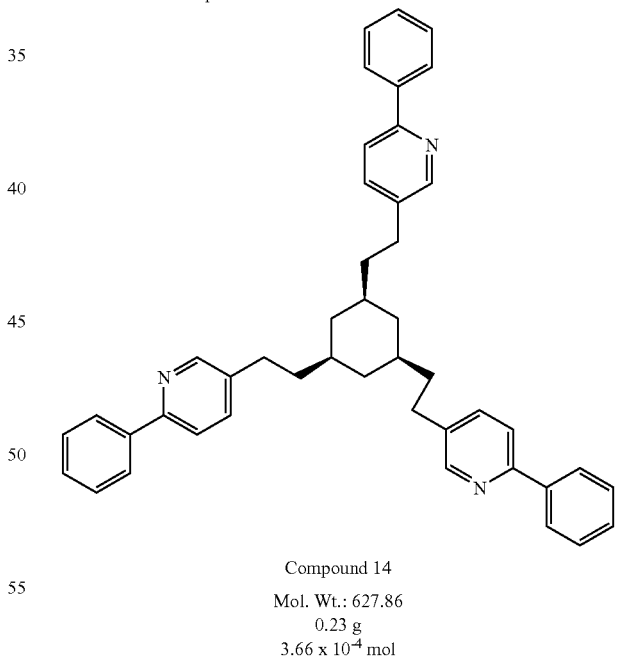

Compound 14
Mol. Wt.: 627.86
0.23 g
3.66 x 10⁻⁴ mol

A reaction was performed in a stream of an inert gas.

A solution of Compound 12 (0.36 g) in THF (2 ml) was slowly dropped to a solution of Compound 13 prepared from Compound 3 obtained in the above item (1) of Example 1 (0.51 g, molecular weight 169.22, 3.01 mmol) and an equivalent of n-butyllithium (1.6-M hexane solution) in THF (3 ml) under ice cooling. After that, the temperature of the reaction liquid was returned to room temperature, and the reaction liquid was subjected to a reaction for 24 hours. After the completion of the reaction, the reaction liquid was poured into ice water, and the whole was extracted with diethyl ether. Next, the diethyl ether solution was dried (dehydrated) with anhydrous magnesium sulfate and filtered, and a volatile component was removed by distillation under reduced pressure, whereby a coarse product was obtained. Further, the coarse product was purified by means of silica gel column chromatography, whereby 0.23 g of Compound 14 as a target in the form of a pale yellow solid was obtained (37% yield).

(6) Synthesis of Compound 15 Compound 15 was synthesized in accordance with the following process.

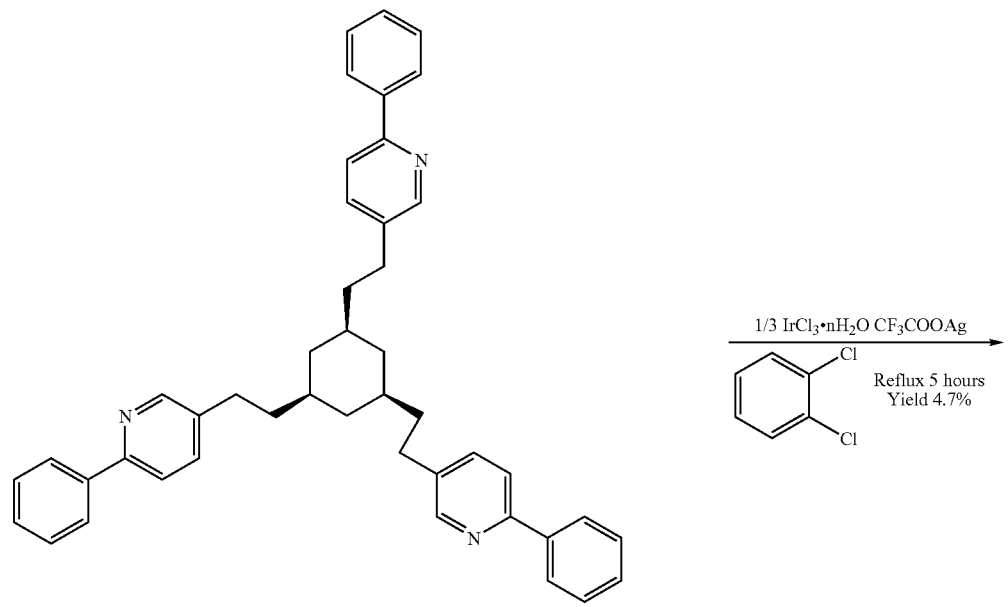

Compound 14
Mol. Wt.: 627.86
0.12 g
$1.91 \times 10^{-4}$ mol

Mol. Wt.: 353
0.071 g
$2.01 \times 10^{-4}$ mol

Mol. Wt.: 220.88
0.18 g
$8.15 \times 10^{-4}$ mol

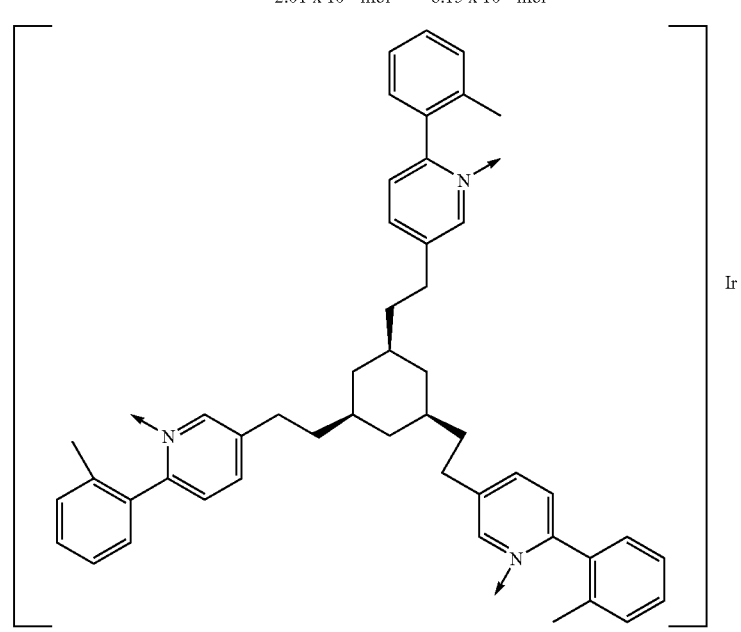

Compound 15
Mol. Wt.: 817.05
0.0074 g
$9.06 \times 10^{-6}$ mol

In a stream of an inert gas, 1 ml of water, 0.12 g (1.91×10⁻⁴ mol) of Compound 14, 0.071 g (2.01×10⁻⁴ mol) of IrCl₃.nH₂O, and 0.18 g (8.15×10⁻⁴ mol) of silver trifluoroacetate were added to 20 ml of 1,2-dichlorobenzene, and the whole was subjected to a reaction under reflux for 5 hours. After that, the temperature of the reaction liquid was cooled to room temperature, and the reaction liquid was passed through a silica gel and filtered (developing solvent: methylene chloride/hexane=50:50). The solvent was removed by distillation, whereby Compound 15 as a target in the form of a yellow solid was obtained (0.0074 g, 4.7% yield).

The following items (1) to (3) of the resultant compound (Compound 15) were measured.

<Various Results of Measurement>

(1) FD-MS measurement: the maximum peak value was 817, and coincided with a calculated value (calculated value M⁺ (molecular ion peak)=817).

The FD-MS measurement (field desorption ionization mass spectrometry) was performed under the following conditions.

Device: HX 110 (manufactured by JEOL Ltd.)

Conditions: acceleration voltage 8 kV scan range m/z=50 to 1,500 emitter kind carbon emitter current 0 mA→2 mA/min→40 mA (held for 10 minutes)

Figure 5:
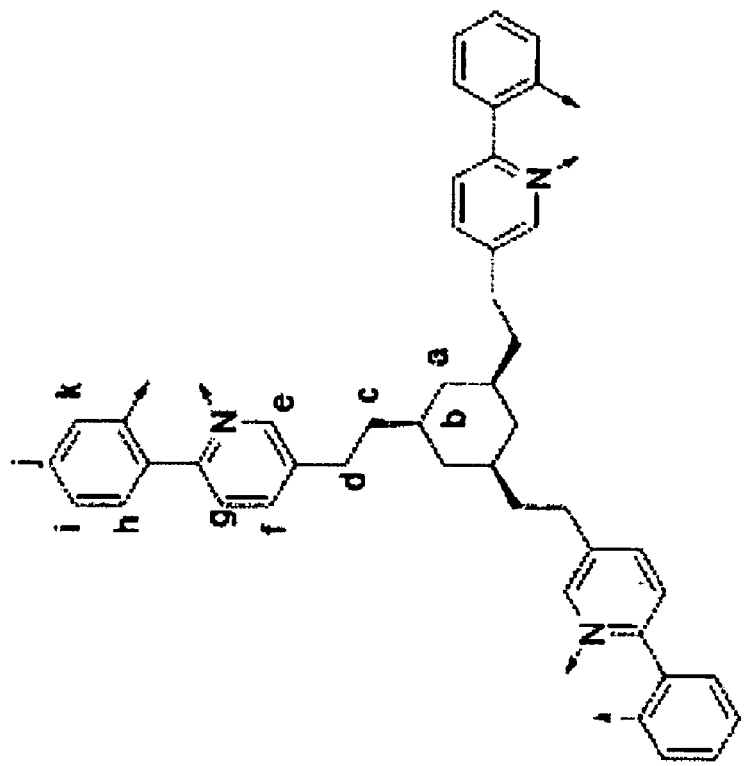
[FIG. 5] A view showing $^1$H-NMR spectrum data on Metal Complex Compound 15 obtained in Example 2.
Figure 6:
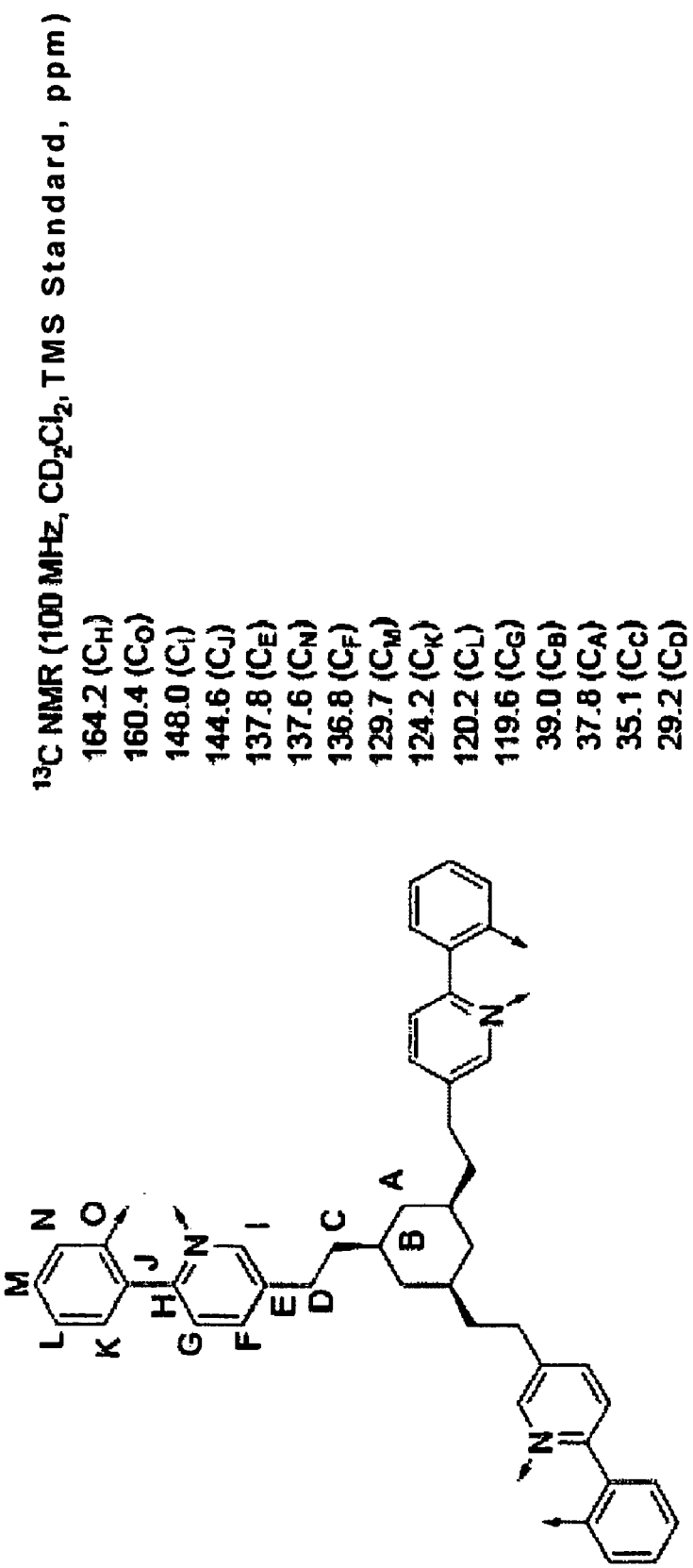
[FIG. 6] A view showing $^{13}$C-NMR spectrum data on Metal Complex Compound 15 obtained in Example 2.

(2) NMR measurement: attribution was performed as described below by $^1$H-NMR, $^{13}$C-NMR, H—H COSY, HMQC, HMBC, and NOESY (FIG. 5: $^1$H-NMR, FIG. 6: $^{13}$C-NMR).

NMR device name: JEOL JNM-ECP 400 ($^1$H-NMR: 400 MHz, $^{13}$C-NMR: 100 MHz)

Measurement solvent: solvent CD₂Cl₂ (deuterated methylene chloride), standard 0.00 ppm (tetramethylsilane)

Figure 7:
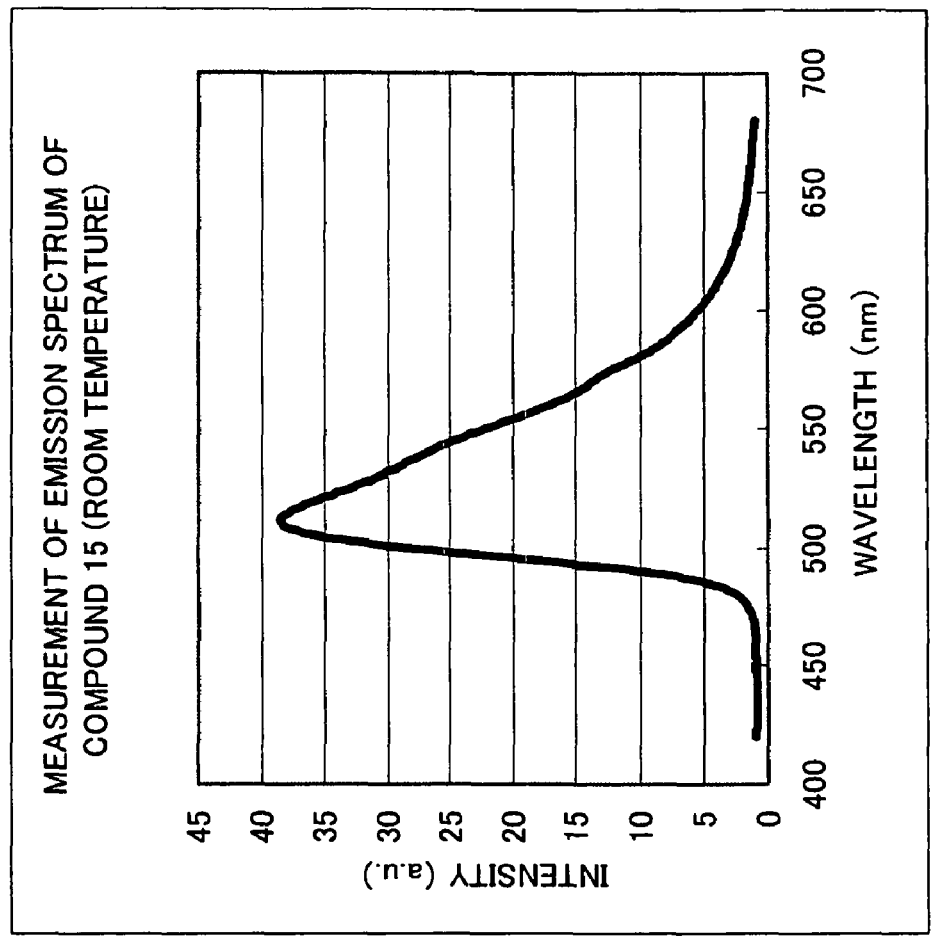
[FIG. 7] A view showing the emission spectrum of Metal Complex Compound 15.

(3) Measurement of emission spectrum (room temperature): see FIG. 7

Device: F-4500 spectrofluorometer

Measurement solvent: methylene chloride

FIG. 7 shows that light was emitted in a solution state (maximum luminous wavelength $\lambda_{max}$=512 nm).

INDUSTRIAL APPLICABILITY

As described above in detail, the organic EL device using the transition metal complex compound of the present invention has high luminous efficiency and a long emission lifetime. In addition, the organic EL device using the transition metal complex compound having a metal carbene bond of the present invention emits blue light, and has high luminous efficiency and a long emission lifetime. Accordingly, the transition metal complex compound is extremely useful as a material for an organic EL device requested to emit blue light.

The invention claimed is:

1. An iridium metal complex compound having a ligand represented by the following general formula (I):

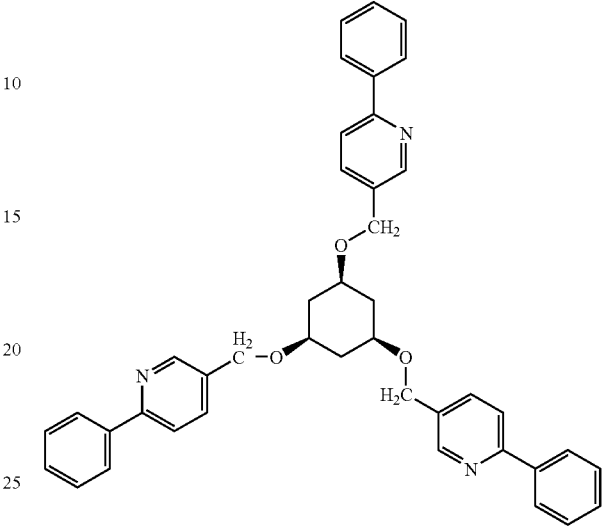

(I)

wherein the phenylpyridinyl groups of the ligand may be substituted or unsubstituted.

2. The iridium metal complex compound according to claim 1, wherein each of the phenylpyridinyl groups is unsubstituted.

3. The iridium metal complex compound according to claim 1, wherein one or more of the phenylpyridinyl groups is substituted with a methyl group at an ortho position on the phenyl group.

4. The iridium metal complex compound according to claim 1, wherein each of the phenylpyridinyl groups is substituted with a methyl group at the ortho position of the phenyl group.

5. The iridium metal complex compound according to claim 1, wherein each of the phenylpyridinyl groups is independently substituted with one or more halogen atoms.

6. The iridium metal complex compound according to claim 1, wherein each of the phenylpyridinyl groups is substituted with one or more halogen atoms.

7. The iridium metal complex compound according to claim 1, wherein each of the phenylpyridinyl groups is fully substituted with fluorine atoms.

8. The iridium metal complex compound according to claim 1, wherein each of the phenyl groups of each of the phenylpyridinyl groups is fully substituted with fluorine atoms.

9. The iridium metal complex compound according to claim 1, wherein each of the phenylpyridinyl groups is independently substituted by one or more selected from the group consisting of an alkyl group having 1 to 10 carbon atoms, a cycloalkyl group having 5 to 7 carbon atoms, an alkoxy group having 1 to 10 carbon atoms, a halogen substituted alkyl group having 1 to 10 carbon atoms, an unsubstituted aryl group, an aryl group substituted with one or more halogen atoms, an aryloxy group having 5 to 50 carbon atoms, an amino group, a nitro group, a hydroxyl group and a carboxyl group.

10. The iridium metal complex compound according to claim 1, wherein one or more of the phenylpyridinyl groups is substituted with one or more groups selected from the group consisting of a methyl group, an ethyl group, a propyl group, a butyl group, a pentyl group, a hexyl group, a cyclopentyl group and cyclohexyl group.

11. An organic electroluminescence device, comprising an organic thin film layer including at least a light emitting layer,
    wherein the organic thin film layer is interposed between an anode and a cathode, and
    wherein at least one layer of the organic thin film layer contains the iridium metal complex compound according to claim 1.

12. The organic electroluminescence device according to claim 11, wherein the light emitting layer contains the iridium metal complex compound as a light emitting material.

13. The organic electroluminescence device according to claim 11, wherein the light emitting layer contains the iridium metal complex compound as a dopant.

14. The organic electroluminescence device according to claim 11, wherein:
    at least one of an electron injecting layer and an electron transporting layer is present between the light emitting layer and the cathode; and
    at least one of the electron injecting layer and the electron transporting layer contains a n-electron-deficient nitrogen-containing heterocyclic derivative as a main component.

15. The organic electroluminescence device according to claim 11, wherein a reducing dopant is present in an interfacial region between the cathode and the organic thin film layer.

* * * * *